US007314478B2

(12) United States Patent
Hui

(10) Patent No.: US 7,314,478 B2
(45) Date of Patent: Jan. 1, 2008

(54) HIGH EFFICIENCY EXTERNAL COUNTERPULSATION APPARATUS AND METHOD FOR CONTROLLING SAME

(75) Inventor: John C. K. Hui, East Setauket, NY (US)

(73) Assignee: Vasomedical, Inc., Westbury, NY (US)

(*) Notice: Subject to any disclaimer, the term of this patent is extended or adjusted under 35 U.S.C. 154(b) by 543 days.

(21) Appl. No.: 11/047,509

(22) Filed: Jan. 31, 2005

(65) Prior Publication Data

US 2005/0131456 A1 Jun. 16, 2005

Related U.S. Application Data

(60) Division of application No. 10/037,974, filed on Nov. 9, 2001, now Pat. No. 6,962,599, which is a continuation-in-part of application No. 09/710,692, filed on Nov. 10, 2000, now Pat. No. 6,589,267.

(51) Int. Cl.
*A61B 17/12* (2006.01)

(52) U.S. Cl. ........................................ 606/202

(58) Field of Classification Search ................ 606/201, 606/202, 203, 204; 601/148, 149, 150, 151, 601/152; 600/16, 17; 128/898
See application file for complete search history.

(56) References Cited

U.S. PATENT DOCUMENTS

| | | | |
|---|---|---|---|
| 2,230,068 | A | 1/1941 | Roensch |
| 2,249,579 | A | 7/1941 | Rea |
| 2,361,242 | A | 10/1944 | Rosett |
| 2,528,843 | A | 11/1950 | Poor |
| 2,533,504 | A | 12/1950 | Poor |
| 2,543,284 | A | 2/1951 | Gleason |
| 2,674,231 | A | 4/1954 | Erickson |
| 2,694,395 | A | 11/1954 | Brown |
| 2,747,570 | A | 5/1956 | Jobst |

(Continued)

FOREIGN PATENT DOCUMENTS

| | | |
|---|---|---|
| DE | 25 44 299 | 4/1977 |

(Continued)

OTHER PUBLICATIONS

E.S. Bucherl et al., Counterpulsation: Foundation and Future, with a Tribute to William Clifford Birtwell (1916-1978), pp. 20-23.

(Continued)

*Primary Examiner*—Kevin T. Truong
(74) *Attorney, Agent, or Firm*—Harness, Dickey & Pierce, P.L.C.

(57) ABSTRACT

A method of controlling an external counterpulsation apparatus includes selecting a patient treatment pressure; outputting a signal corresponding to the selected treatment pressure; detecting a pressure of a compressed fluid reservoir; comparing the selected treatment pressure to the compressed fluid reservoir pressure; and controlling a pressure regulator valve based on a difference between the patient treatment pressure and the compressed fluid reservoir pressure. The compressed fluid reservoir pressure may be decreased when the compressed fluid reservoir pressure is greater than a preset difference from the patient treatment pressure, particularly by venting the compressed fluid reservoir to atmosphere. The compressed fluid reservoir pressure may be necessary when the compressed fluid reservoir pressure is less than a preset difference from the patient treatment pressure, particularly by operating a compressor.

12 Claims, 26 Drawing Sheets

U.S. PATENT DOCUMENTS 3,063,444 A 11/1962 Jobst
3,094,116 A 6/1963 Logan et al.
3,179,106 A 4/1965 Meredith
3,303,841 A 2/1967 Dennis
3,403,673 A 10/1968 MacLeod
3,483,862 A 12/1969 Takeuchi
3,548,809 A 12/1970 Conti
3,654,919 A 4/1972 Birtwell
3,659,593 A 5/1972 Vail
3,712,290 A 1/1973 Imich et al.
3,734,087 A 5/1973 Sauer et al.
3,783,859 A 1/1974 Sauer et al.
3,786,802 A 1/1974 Hagopian et al.
3,795,242 A 3/1974 Lerch et al.
3,835,845 A 9/1974 Maher
3,859,989 A 1/1975 Spielberg
3,862,629 A 1/1975 Rotta
3,865,103 A 2/1975 Folman
3,866,604 A 2/1975 Curless et al.
3,878,839 A 4/1975 Norton et al.
3,892,229 A 7/1975 Taylor et al.
3,901,221 A 8/1975 Nicholson et al.
3,942,518 A 3/1976 Tenteris et al.
3,961,625 A 6/1976 Dillon
3,970,076 A 7/1976 Hepp et al.
3,976,056 A 8/1976 Brawn
4,013,069 A 3/1977 Hasty
4,030,488 A 6/1977 Hasty
4,077,402 A 3/1978 Benjamin, Jr. et al.
4,080,958 A 3/1978 Bregman et al.
4,091,804 A 5/1978 Hasty
4,135,496 A 1/1979 Chazov et al.
4,253,449 A 3/1981 Arkans et al.
4,269,175 A 5/1981 Dillon
4,343,302 A 8/1982 Dillon
4,388,919 A 6/1983 Benjamin, Jr. et al.
4,454,494 A 6/1984 Williams et al.
4,481,937 A 11/1984 Arkans
4,590,925 A 5/1986 Dillon
4,738,249 A 4/1988 Linman et al.
4,753,226 A 6/1988 Zheng et al.
4,971,042 A 11/1990 Lerman
5,000,164 A 3/1991 Cooper
5,090,417 A 2/1992 Mollan et al.
5,095,912 A 3/1992 Tomita
5,109,832 A 5/1992 Proctor et al.
5,245,990 A 9/1993 Bertinin
5,429,584 A 7/1995 Chiu
5,443,440 A 8/1995 Turney et al.
5,487,722 A 1/1996 Weaver, II et al.
5,490,820 A 2/1996 Schock et al.
5,514,079 A 5/1996 Dillon
5,554,103 A 9/1996 Zheng et al.
5,571,075 A 11/1996 Bullard
5,840,049 A 11/1998 Tumey et al.
5,891,012 A 4/1999 Downey et al.
5,891,062 A 4/1999 Schock et al.
5,951,502 A 9/1999 Peeler et al.
5,997,540 A 12/1999 Zheng et al.
6,120,431 A 9/2000 Magovern et al.
6,132,363 A 10/2000 Freed et al.
6,144,880 A 11/2000 Ding et al.
6,161,038 A 12/2000 Schookin et al.
6,355,008 B1 3/2002 Nakao
6,371,123 B1 4/2002 Stark et al.
6,450,942 B1 9/2002 Lapanashvili et al.
6,450,981 B1 9/2002 Shabty et al.
6,572,621 B1 6/2003 Zheng et al.
6,589,267 B1 7/2003 Hui
6,620,116 B2 9/2003 Lewis
6,645,165 B2 11/2003 Waldridge et al.
6,736,786 B1 5/2004 Shabty et al.
6,752,771 B2 6/2004 Rothman et al.
6,770,041 B2 8/2004 Rastegar et al.
6,786,879 B1 9/2004 Bolam et al.
7,074,177 B2 * 7/2006 Pickett et al. ............... 606/202
2001/0018563 A1 8/2001 Waldridge et al.
2001/0027279 A1 10/2001 Rothman et al.
2002/0103454 A1 8/2002 Sackner et al.
2002/0111571 A1 8/2002 Warwick et al.
2002/0115949 A1 8/2002 Kuslich et al.
2002/0169399 A1 11/2002 Rastegar et al.
2002/0173735 A1 11/2002 Lewis
2002/0178030 A1 11/2002 Loeb
2003/0009115 A1 1/2003 Sherman et al.
2003/0009119 A1 1/2003 Kamm et al.
2003/0028131 A1 2/2003 Van Brunt et al.
2003/0032904 A1 2/2003 Egger
2003/0050551 A1 3/2003 Shabty et al.
2003/0125649 A1 7/2003 McIntosh et al.
2003/0176822 A1 9/2003 Morgenlander
2003/0191420 A1 10/2003 Kuiper et al.
2003/0191437 A1 10/2003 Knighton et al.
2003/0200971 A1 10/2003 Rastegar et al.
2003/0204151 A1 10/2003 Rastegar et al.
2003/0205230 A1 11/2003 Shusterman et al.
2003/0216651 A1 11/2003 Burns et al.
2003/0216672 A1 11/2003 Rastegar et al.
2003/0233118 A1 12/2003 Hui
2004/0010212 A1 1/2004 Kuiper et al.
2004/0054306 A1 3/2004 Roth et al.
2004/0064077 A1 4/2004 Dillon
2004/0102675 A1 5/2004 Peters et al.
2004/0106884 A1 6/2004 Bolam et al.
2004/0106885 A1 6/2004 Shabty et al.
2004/0116840 A1 6/2004 Cantrell et al.
2004/0138596 A1 7/2004 Joze et al.
2004/0162493 A1 8/2004 Mills
2004/0167580 A1 8/2004 Mann et al.
2004/0199090 A1 10/2004 Sanders et al.
2004/0210176 A1 10/2004 Diana
2004/0230090 A1 11/2004 Hegde et al.
2004/0254482 A1 12/2004 Anderson et al.
2004/0260217 A1 12/2004 Gardner et al.
2004/0260218 A1 12/2004 Shah et al.
2005/0004497 A1 1/2005 Dehli

FOREIGN PATENT DOCUMENTS

EP 0203310 3/1986
EP 1 078 649 2/2001
FR 1562252 2/1969
JP 11-19145 1/1999
WO WO 99/086444 2/1999

OTHER PUBLICATIONS

W. Birtwell et al., Transactions—American Society for Artificial Internal Organs, vol. XI, 1965, pp. 43-51.

Lawrence S. Cohen, MD, FACC, et al., Sequenced External Counterpulsation and Intraaortic Balloon Pumping in Cardiogenic Shock, Oct. 1973, The American Journal of Cardiology, vol. 32, pp. 656-661.

W. C. Birtwell et al., The Present Status of External Counterpulsation, 1979, pp. 71-78.

Juan Lin et al., An Analytical Approach to the Determination of Optimal Phasing for External Counterpulsation, Journal of Bioengineering vol. 2, 1978, pp. 167-175.

Zhen-sheng Zheng et al., Sequential External Counterpulsation (SECP) in China, Transactions of the American Society Artificial Internal Organs, 1983; 29:599-603.

William E. Lawson, MD et al., Enhanced External Counterpulsation for Chronic Myocardial Ischemia, The Journal of Critical Illness, vol. 15, No. 11, Nov. 2000.

William E. Lawson et al., Treatment Benefit in the Enhanced External Counterpulsation Consortium, General Cardiology, Cardiology 2000; 94:31-35.

The Journal of Heart Disease, Abstracts, May 1999, vol. 1, No. 1, 4 pages.

Supplement to Journal of the American College of Cardiology, 49th Annual Scientific Session, Feb. 2000, 2 pp.

Program & Abstracts, The Endocrine Society's 82nd Annual Meeting, Jun. 21-24, 2000, 2 pp.

Jay N. Cohn Supplement to Journal of Cardiac Failure, vol. 16, No. 3, Sep. 2000, 4 pp.

Abstracts from Scientific Sessions 2000, Supplement to Journal of the American Heart Association, Nov. 12-15, 2000, 2 pp.

British Cardiac Society Annual Conference, May 2001, vol. 85, Supplement 1, 3 pp.

Hisashi Urano, MD et al., Enhanced External Counterpulsation Improves Exercise Tolerance, Journal of the American College of Cardiology, Jan. 2001, vol. 37, No. 1, pp. 93-97.

William E. Lawson, MD et al., Enhanced External Counterpulsation for Chronic Myocardial Ischemia, Critical Procedures: No. 138, The Journal of Critical Illness, vol. 15, Issue 11, Nov. 2000, 8 pp.

Ozlem Soran, MD et al., Enhanced External Counterpulsation in the Management of Patients with Cardiovascular Disease, Clin. Cardiol. 22, 173-178 (1999).

* cited by examiner

Range for $T_1$: $150ms \leq T_1 \leq (T_x - 200ms)$

Range for $T_2$: $(T_1 + 150ms) \leq T_2 \leq (T_R - 30ms)$

HIGH EFFICIENCY EXTERNAL COUNTERPULSATION APPARATUS AND METHOD FOR CONTROLLING SAME

CROSS-REFERENCE TO RELATED APPLICATIONS

This application is a divisional of U.S. patent application Ser. No. 10/037,974 filed on Nov. 9, 2001, now U.S. Pat. No. 6,962,599 which is a continuation-in-part of U.S. patent application Ser. No. 09/710,692 filed on Nov. 10, 2000 now U.S. Pat. No. 6,589,267. The disclosures of the above applications are incorporated herein by reference.

DISCUSSION OF THE INVENTION

The present invention relates to an external counterpulsation apparatus and method for controlling the same and, more particularly, to such an external counterpulsation apparatus and method for controlling the same having improved efficiency and utility.

External counterpulsation is a noninvasive, atraumatic means for assisting and increasing circulation in patients. External counterpulsation uses the patient's physiological signals related to their heart cycle (e.g., electrocardiograph (ECG), blood pressure, blood flow) to modulate the inflation and deflation timing of sets of compressive cuffs wrapped around a patient's calves, lower thighs and/or upper thighs, including the lower buttocks. The cuffs inflate to create a retrograde arterial pressure wave and, at the same time, push venous blood return from the extremities to reach the heart at the onset of diastole. The result is augmented diastolic central aortic pressure and increased venous return. Rapid, simultaneous deflation of the cuffs produces systolic unloading and decreased cardiac workload. The end results are increased perfusion pressure to the coronary artery during diastole, when the heart is in a relaxed state with minimal resistant to blood flow; reduced systolic pressure due to the "sucking effect" during cuff deflation; and increased cardiac output due to increased venous return and reduced systolic pressure.

Under normal operating conditions, when the heart contracts and ejects blood during systole, the aortic and coronary perfusion pressure increases. It should also be noted that the workload of the heart is proportional to the systolic pressure. However, during systole the impedance to coronary flow also increases significantly due to the contracting force of the myocardium, thereby restricting coronary blood flow. Also, during diastole, the myocardium is in a relaxed state, and impedance to coronary flow is significantly reduced. Consequently, although the diastolic perfusion pressure is much lower than systolic pressure, the coronary blood flow during diastole accounts for approximately eighty (80) percent of the total flow.

The historical objectives of external counterpulsation are to minimize systolic and maximize diastolic pressures. These objectives coalesce to improve the energy demand and supply ratio. For example, in the case of patients with coronary artery disease, energy supply to the heart is limited. External counterpulsation can be effective in improving cardiac functions for these patients by increasing coronary blood flow and therefore energy supply to the heart.

During a treatment session, the patient lies on a table. Electronically controlled inflation and deflation valves are connected to multiple pairs of inflatable devices, typically adjustable cuffs, that are wrapped firmly, but comfortably, around the patient's calves, lower thighs, and/or upper thighs, including the buttocks. The design of the cuffs permits significant compression of the arterial and venous vasculature at relative low pneumatic pressures (200-350 millimeters Hg).

The earlobe pulse wave, finger pulse finger or temporal pulse wave is used as a timing signal to give the appropriate time for application of the external pressure so that the resulting pulse produced by external pressure in the artery can arrive at the root of the aorta just at the closure of the aortic valve. Thus, the arterial pulse wave is divided into a systolic period and a diastolic period. The earlobe pulse wave, finger pulse wave or temporal pulse wave signals, however, may not reflect the true pulse wave from the great arteries such as the aorta.

According to the present invention, there are two factors that should be taken into account to determine the appropriate deflation time of all the inflatable devices: (1) release of all external pressure before the next systole to produce maximal systolic unloading, i.e., the maximum reduction of systolic pressure; (2) maintenance of the inflation as long as possible to fully utilize the whole period of diastole so as to produce the longest possible diastolic augmentation, i.e., the increase of diastolic pressure due to externally applied pressure. One measurement of effective counterpulsation is the ability to minimize systolic pressure, and at the same time maximize the ratio of the area under the diastolic wave form to that of the area under the systolic wave form. This consideration can be used to provide a guiding rule for determination of optimal deflation time.

Furthermore, the various existing external counterpulsation apparatuses only measure the electrocardiographic signals of the patient to guard against arrhythmia. Because counterpulsation applies pressure on the limbs during diastole, which increases the arterial pressure in diastole and makes it higher than the systolic pressure, the blood flow dynamics and physiological parameters of the human body may vary. Some of these variations are beneficial.

An external counterpulsation apparatus according to the invention generally includes a plurality of inflatable devices adapted to be received about the lower extremities of the patient, a source of compressed fluid in communication with the plurality of inflatable devices, and a fluid distribution assembly interconnecting the source of compressed fluid and the inflatable devices. The fluid distribution assembly includes a selectively operable inflation/deflation valve interconnected between each of the inflatable devices and the source of compressed fluid. The fluid distribution assembly distributes compressed fluid from the source of compressed fluid to the inflation/deflation valve and operates each inflation/deflation valve to sequentially inflate and deflate each of the inflatable devices. Each inflation/deflation valve has in input in fluid communication with the source of compressed fluid, an inflation/deflation port in fluid communication with one of the inflatable devices, and a deflation exhaust port in fluid communication with the atmosphere. The deflation exhaust port is normally open so as to exhaust compressed fluid upon loss of power to the external counterpulsation apparatus.

The source of compressed may include a compressor and a power ramp-up device. The power ramp-up device, upon startup of the apparatus, converts electrical power to the compressor from 110/120 VAC 50/60 Hz to three-phase 220 VAC at a variable frequency. The power ramp-up device also increases the electrical power to a preselected full power level over a period of approximately three to five seconds.

In an external counterpulsation apparatus according to the invention, a treatment table is provided upon which the patient Is situated during the treatment. The treatment table includes a main portion and an articulating portion selectively adjustable to a plurality of angulated positions relative to the main portion. The treatment table further includes a motor-driven elevation assembly actuable to selectively raise and lower the treatment table to a plurality of different elevated positions. The treatment table further includes a plurality of wheels allowing the treatment table to be selectively moved between a plurality of locations.

The treatment table may further include an inflation/deflation valve mounted to the treatment table and movable therewith. The inflation/deflation valve selectively inflates and deflates an inflatable device attachable to the patient.

DETAILED DESCRIPTION OF THE PREFERRED EMBODIMENTS

A detailed description of varied and merely exemplary embodiments of the present invention follows with reference to the accompanying drawings. One skilled in the art will readily recognize that the principles of the invention are equally applicable to other embodiments and applications.

Figure 1:
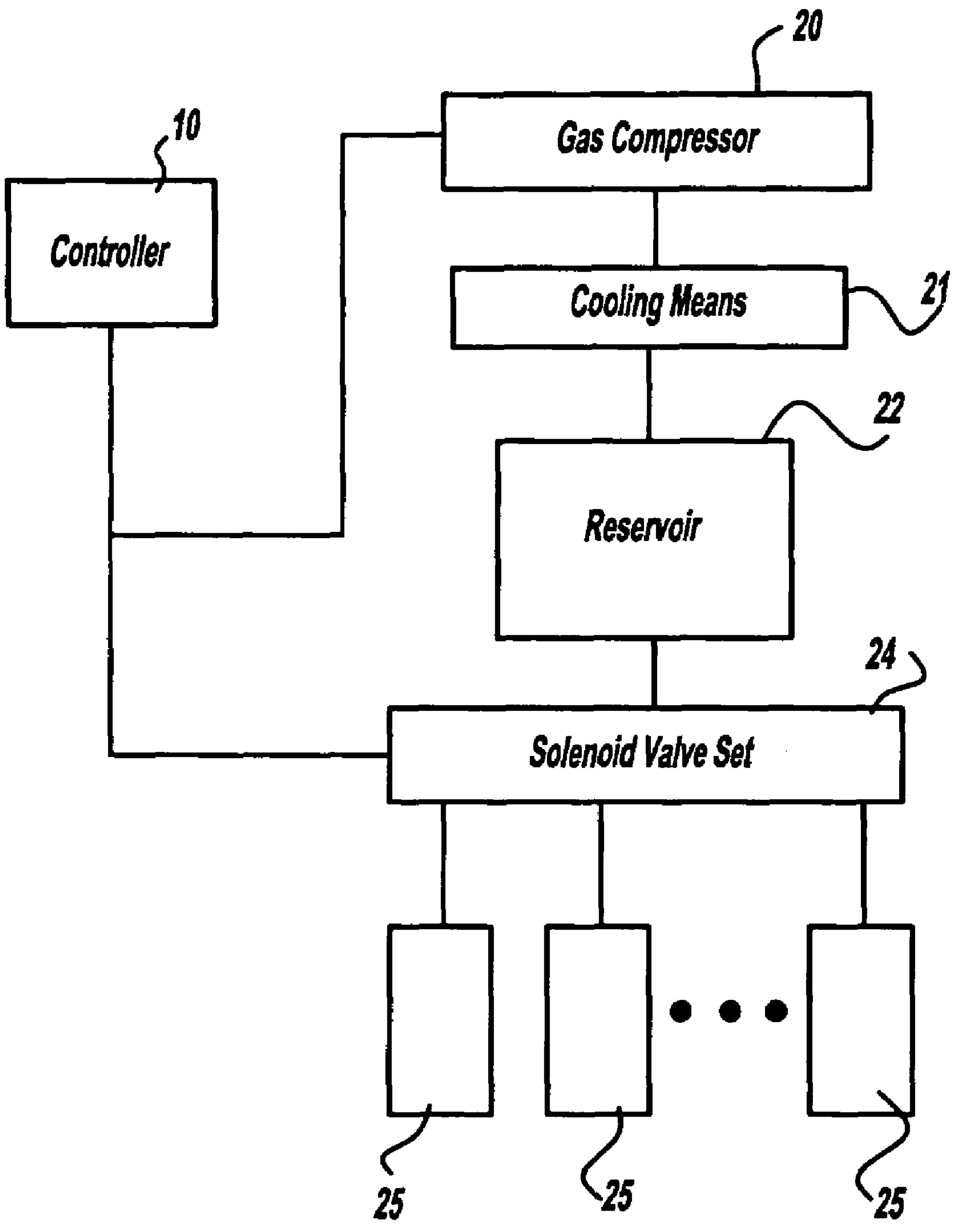
FIG. 1 is a block diagram of an external counterpulsation apparatus according to the present invention.

FIG. 1 is a block diagram of a first exemplary embodiment of an external counterpulsation apparatus according to the present invention, wherein a controller 10 controls the gas compressor 20 and set of solenoid valves 24. The compressor can be of rotary vane, piston, diaphragm or blower type. One suitable compressor is a scroll-type compressor as described in U.S. Pat. No. 5,554,103, commonly assigned and incorporated herein by reference, which essentially consists of two scroll basin with very narrow gaps between them; with one scroll basin adapted to rotate at very high speed (3,000 rpm) while the other scroll basin remains stationary. The clenching of the scroll basins compresses the air radially inwardly toward the center and the compressed air comes out of the center shaft. During operation, the compressor 20 operates to produce pressurized gas, such as pressurized air, which is sent into the positive pressure reservoir 22 via a cooling means 21. A pressure-limiting valve 23 is provided on the reservoir 22, which keeps the internal pressure of the reservoir 22 constant. For this variation of the invention, the opening and closing of the set of solenoid valves 24 is, controlled by the inflation and deflation driving signals generated by the controller 10. The set of solenoid valves 24 may include a number of two-position, three-way solenoid valves corresponding to the number of inflatable devices 25. When a valve is in the first of the two positions, it inflates the inflatable device; when it is in the second of the two positions, it deflates the inflatable device, under control of the control system. Other valve assemblies, including those disclosed below, may be used in accordance with the invention. Each inflatable device. 25 may include a balloon or air bladder surrounded by a cuff, or may be unitary in structure. The inflatable devices 25 may include cuffs wrapped tightly around the lower limbs with inflatable devices 25 put in between the cuffs and the body. When compressed gas is injected into the inflatable devices 25, the cuff will also expand and extend outward, due to the elasticity and extensibility of its material. Suitable cuff and balloon apparatuses shown and described in U.S. Pat. No. 5,554,103, are incorporated herein by reference. More or fewer inflatable devices 25 may be used, but three are shown here for explanation purposes. For example, more devices may be used to improve the fit, and thus the effectiveness of counterpulsation.

Figure 2:
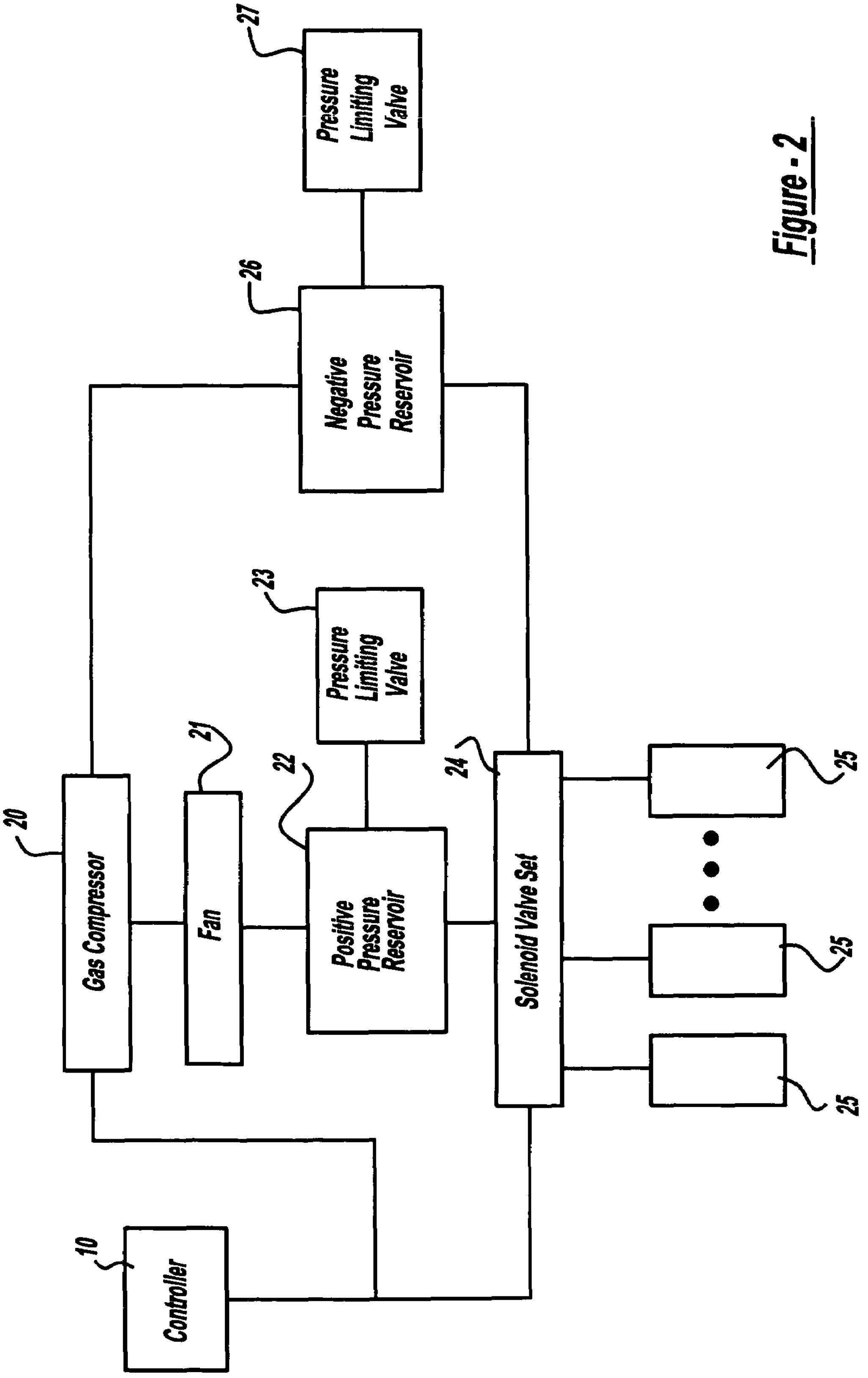
FIG. 2 is a block diagram of an external counterpulsation apparatus according to the present invention.

FIG. 2 illustrates another external counterpulsation apparatus according to the present invention. In this variation, a control signal generated by the controller 10 signals the compressor 20 to compress gas into the positive pressure reservoir 22 after being cooled by the cooling means 21. A pressure-limiting valve 23 is provided on the positive pressure reservoir to keep its internal pressure constant. A negative pressure reservoir 26 connected to the inlet of the compressor 20 is a source of negative pressure. The control system 10 controls the opening and closing of the set of solenoid valves 24 by issuing inflation and deflation control signals in accordance with the results of detection. When the set of solenoid valves 24 are in the first position, they inflate the inflatable devices 25, when they are in the second position, they deflate the inflatable devices 25. The gas discharged from the inflatable devices is discharged into the negative pressure reservoir 26 via the set of solenoid valves 24, and then returns to the compressor 20. As there may be leakage during the circulation of gas, which may affect the amount of gas output from the compressor 20, a pressure-limiting valve 27 is provided to adjust the negative pressure in the negative pressure reservoir 26. When the negative pressure exceeds a certain value, the pressure-limiting valve 27 is opened to inject a certain amount of gas into the negative pressure reservoir 26.

Figure 3:
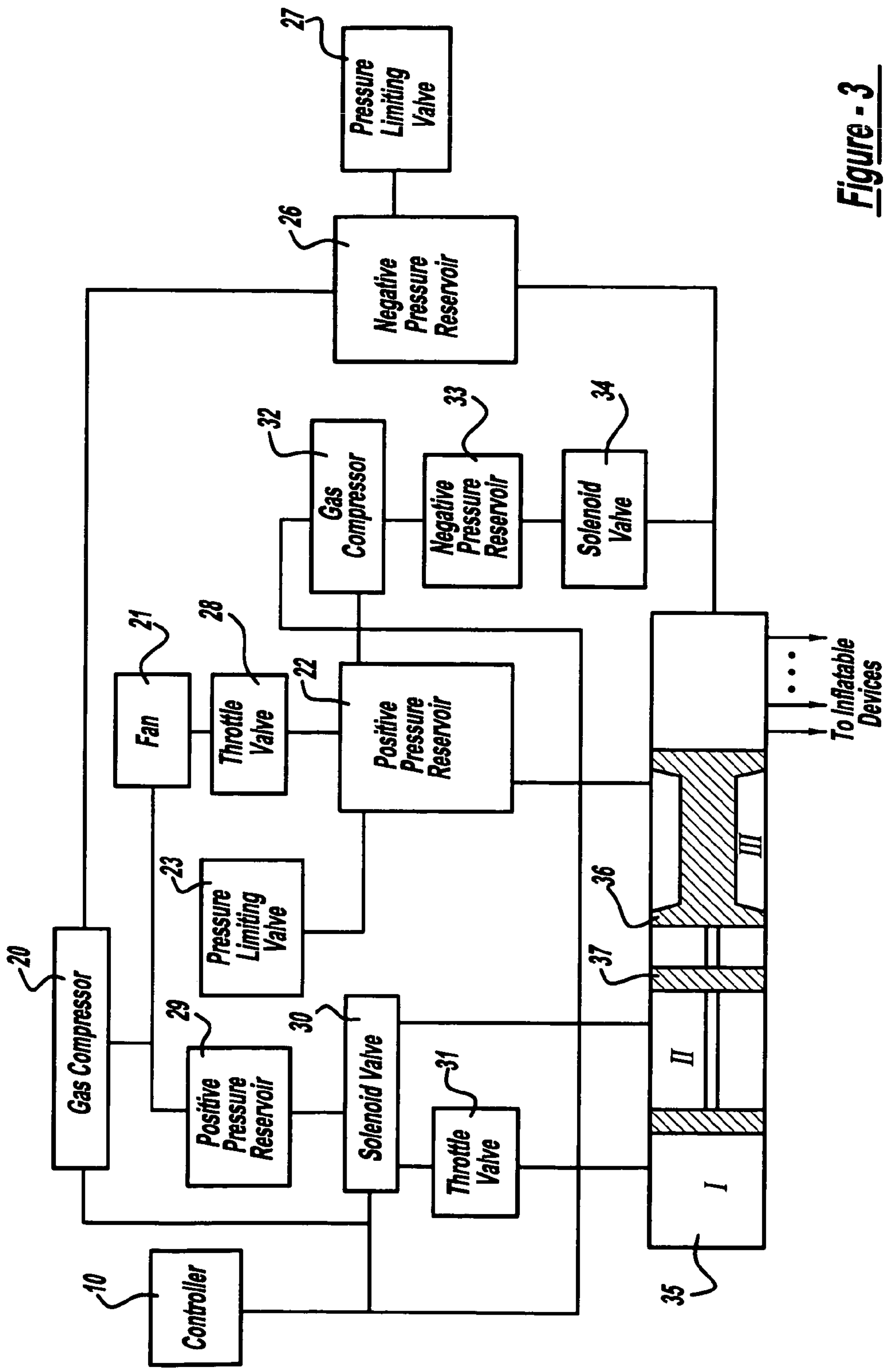
FIG. 3 is a block diagram of an external counterpulsation apparatus according to the present invention.

FIG. 3 illustrates another external counterpulsation apparatus according to the present invention, wherein the controller 10 generates control signals and the compressor 20 operates to produce two portions of pressurized gas, one portion of pressurized gas is sent to the positive pressure reservoir 29, while another is sent into the positive pressure reservoir 22 via the cooling means 21 and a throttle valve 28. The pressure limiting valve 23 is operative to adjust the pressure inside the reservoir 22. The reference numeral 30 indicates a two-position-five-way solenoid valve or two two-position-three-way solenoid valves, 31 indicates a mono-directional throttle valve, 35 indicates a cylindrical gas distribution means or cylinder, 37 is a partition, and 36 indicates a piston. When an inflation driving signal is issued by the controller 10, the solenoid valve 30 opens to the first of the two positions, and the gas flow is introduced into the portion I of the cylinder from the reservoir 29 via the solenoid valve 30 and the throttle governor 31 to push the piston from a first towards a second end of the cylinder 35. A space portion III is formed by the piston 36 and the cylinder 35 and is always in communication with the reservoir 22. Vents for the inflatable devices 25 are situated in sequence in the cylinder 35, the inflatable devices 25 being sequentially inflated as the piston 36 moves towards the second end of the cylinder 35. When a deflation signal is issued by the controller 10, the solenoid valve 30 is moved to its second position, and the gas in the reservoir 29 enters portion 11 of the cylinder 35 via the solenoid valve 30 to push the piston 36 back to the first end of the cylinder 35. At that time, the gas in portion I is discharged via the solenoid valve 30, and the gas in the inflatable devices 25 is discharged to the negative pressure reservoir 26. In order to speed of deflation, a solenoid valve 34 is also opened at the same time and the gas discharged from the inflatable device 25 is discharged to both negative pressure reservoirs 26, 33. Negative pressure reservoir 33 is kept at a negative pressure by the input portion of compressor 32. Discharged gas is also sent to the reservoir 22 by the output portion of the compressor 32.

During the deflation phase, in such an embodiment, if the pressurized inflatable devices 25 is simply exhausted into the atmosphere, exhaustion of the inflatable devices may not be completed, with the residual gas pressing on the tissue mass surrounded by the inflatable devices, reducing the much needed vascular space in the body to receive the volume of blood ejected by the heart. This can reduce the ability of external counterpulsation to unload systolic blood pressure and reduce cardiac workload. The addition of negative pressure reservoirs 26, 33 serve to more rapidly evacuate the pressurized gas in the inflatable devices 25, thereby ensuring complete absence of pressure on the lower extremities, enabling the vasculature that has been previously compressed and emptied during the diastolic period to act as a source of suction to help the heart eject blood and unload systolic blood pressure. In addition, the negative pressure reservoirs 26, 33 ensure the smooth operation of the solenoid valves 30,34 and prevent the leakage of large volumes of pressurized gas exhausting into the atmosphere. This closed gas system also reduces noises generated by the opening and closing of solenoid valves and movement of air from escaping the system. It should be noted, however, that a negative pressure reservoir might not necessarily be required in each variation, embodiment or application of the present invention.

Furthermore, during normal operation of external counterpulsation, there is always some leakage of compressed air from the inflatable device 25 during the inflation period. To compensate for this leakage and to ensure there is adequate air supplied to the compressor 20 for producing air pressure in the range of five (5) to fifteen (15) psi, leakage compensation might be required, such as the use of a vacuum limiting valve, a vacuum pump, or compressor, or some combination thereof. An example of the leakage compensation means is a vacuum limiting valve 27 connected to the negative pressure reservoir 26, set at approximately negative 100 mm Hg. When the negative pressure reservoir is less than approximately 100 mm Hg, the vacuum-limiting valve 27 is open and air is sucked into the reservoir 26 to provide more air to the intake of the compressor 20.

One variation of the present invention includes a gas cylindrical distribution system 35, as shown in FIG. 3, including a syringe-type system to push a piston in one direction to provide sequential inflation of the inflatable devices 25, with the inflatable devices 25 furthest from the heart being inflated first. The inflatable device openings are placed on both sides of the cylinder, connecting to the left and right limbs as well as buttock. The number of inflatable devices can be two (2) to eight (8) or more on each side, but more or fewer may be used. This is achieved by connecting the inflatable devices 25 furthest from the heart to the portion of the cylinder closest to the piston 36, as the piston 36 moves from left to right as shown in FIG. 3. This gas distribution system uses compressed air to move the piston 36 back and forth along cylinder 35, producing a quiet operation without requiring much power. The solenoid valve 30 is a normally open valve to portion 11 of the cylinder 35, thereby connecting portion 11 to the positive pressure reservoir 29 in case of power failure, moving the piston 36 to the left in FIG. 3, exposing all the inflatable devices 25 to the negative pressure reservoir 26, thereby deflating all inflatable devices 25 and reducing the possibility of inducing trauma to the patient.

When air is compressed, heat will be generated. In external counterpulsation, approximately twenty-five (25) cubic feet of air is compressed to five (5) to fifteen (15) psi pressure, generating a gas with temperature reaching as high as seventy (70) to ninety (90) degrees Celsius, depending on the environment and efficiency of the compressor. When compressed gas with such high temperature is sent to the inflatable devices 25, which are in close contact with the patient's skin, it may produce abrasion or burn to the skin, or at least, an uncomfortable feeling to the patient. Therefore, in some embodiments of the invention, cooling the compressed air is preferred. In general, any means of cooling can be utilized in this invention, including exposing to the atmosphere a long piece of coil or metal pipe connecting the compression means to the positive pressure reservoir, blowing air through a coil of metal pipe carrying the heated gas, water cooling such as that used in the radiator of automobile, running cooling water, or air conditioner, for examples.

Figure 4A:
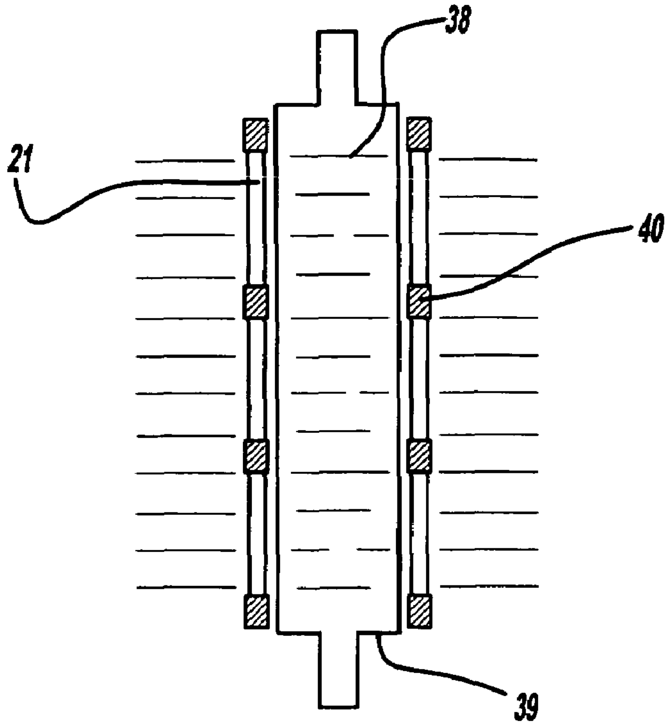
FIGS. 4A and 4B are partial schematic diagrams of a portion of the fluid distribution assembly according to the present invention, illustrating fluid pipes connected to a semiconductor cooling device and air-conditioner cooling evaporator, respectively.
Figure 4B:
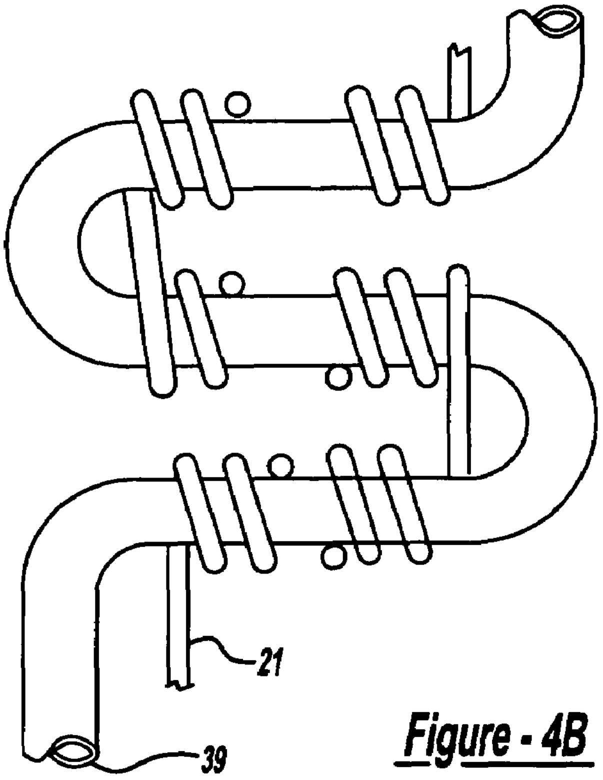

Further cooling examples are shown in FIGS. 4A and 4B which are partial schematic diagrams of the fluid distribution assembly of the external counterpulsation apparatus according to the present invention, illustrating a gas pipe 39 connected to a cooling means. The pipe 39 may be associated with fans 38 and/or heat isolation materials 40, as shown in FIG. 4A, wherein cooling means 21 includes semiconductor-type heat isolation materials 40. In FIG. 4B, the cooling means is an evaporator, i.e., fluid-cooled tubing. Alternatively, the cooling means 21 can be a fan, as shown in FIG. 2. Any other suitable cooling mechanism can be used.

Figure 5:
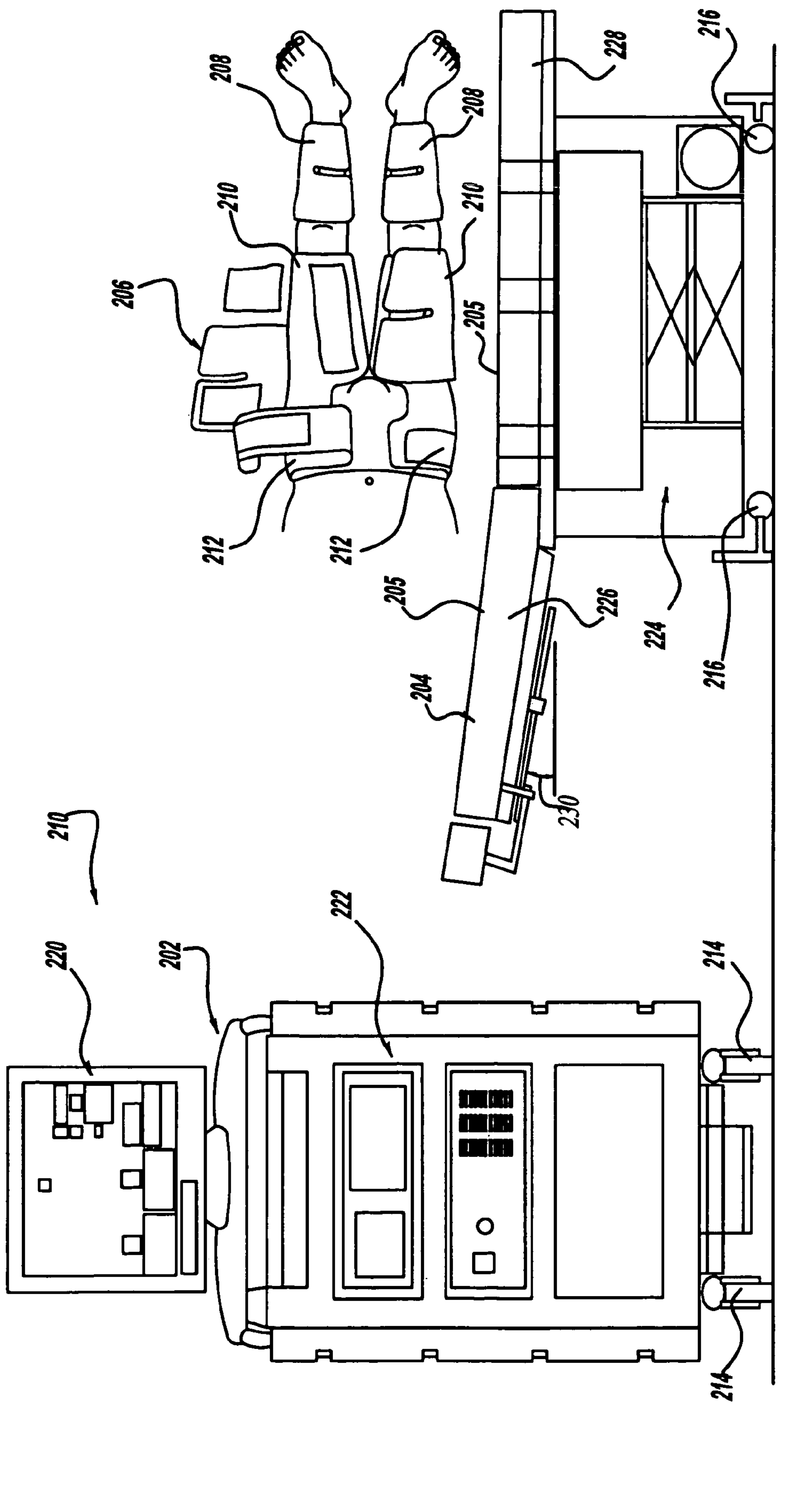
FIG. 5 is a diagrammatic view of an external counterpulsation apparatus according to the present invention.

Beginning with FIG. 5, another embodiment of the external counterpulsation apparatus according to the invention is illustrated and described. External counterpulsation apparatus 201 includes three component assemblies, namely, a control console assembly 202, a treatment table assembly 204, and an inflation/deflation assembly 206. The control console assembly 202 is mounted for mobility from one location to another upon wheels 214, and similarly the treatment table assembly 204 is mounted for mobility from one location to another upon wheels 216. As used herein the term "wheels" includes casters, rollers, track-type belts, or other lockable and unlockable wheel-type devices configured for allowing the components to be "wheeled" from one location to another and then locked in order to maintain the desired position or location. The control console assembly 202 generally includes a user interface device, such as a computer monitor or touch screen 220, and a cabinet or housing 222, in which various components described below are located and housed.

The treatment table assembly 204 generally includes an upper surface 205 on an articulating portion 226 and a horizontal portion 228, with the articulating portion 226 being hingedly or otherwise pivotally interconnected with the horizontal portion 228 for adjustment (either manually or by way of a power drive) to a plurality of angulated positions relative to the horizontal portion 228. In this regard, it should be noted that the angulated position of the articulating portion 226 relative to the horizontal portion 228 is preferably limited to an angle 230 that is thirty (30) degrees above the horizontal. Thus, by way of the motor-driven elevation assembly 224 and the articulating portion 226 of the treatment table assembly 204, a patient receiving treatment can be easily positioned or situated on the upper surface 205, elevated to a desired treatment height, and made comfortable by adjusting the articulating portion 226 relative to the horizontal main portion 228. In this regard, it should be noted that the motor-driven elevation assembly 224 preferably includes a limiting switch or other limiting device (not shown) that limits the elevation of the top or upper surface of the horizontal main portion 228 of the treatment table between heights of twenty-four (24) inches and thirty-six (36) inches from the floor or other surface upon which the treatment table assembly 204 is situated.

Figure 6:
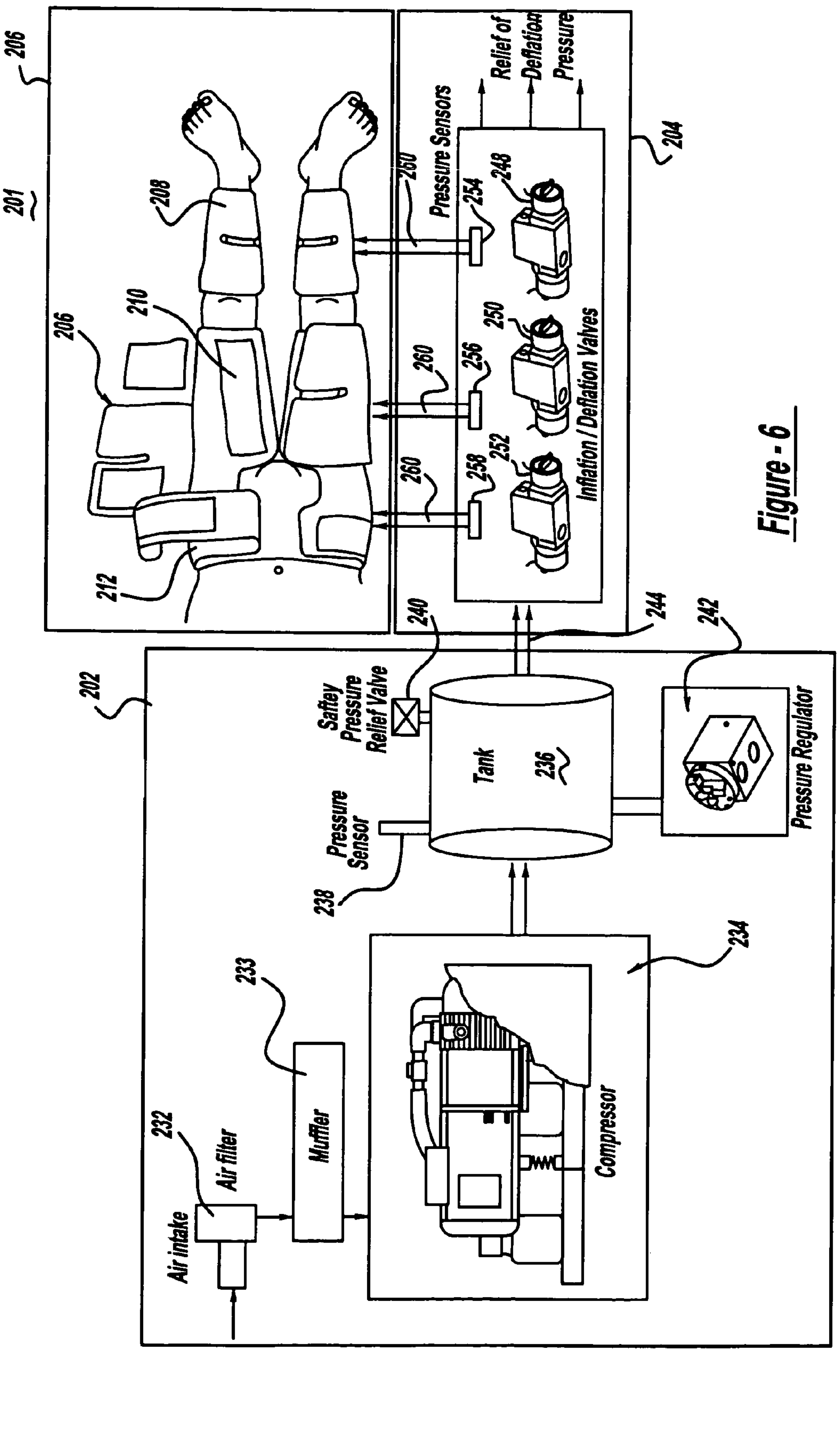
FIG. 6 is a diagrammatic representation of fluid flow of the external counterpulsation apparatus of FIG. 5.
Figure 7:
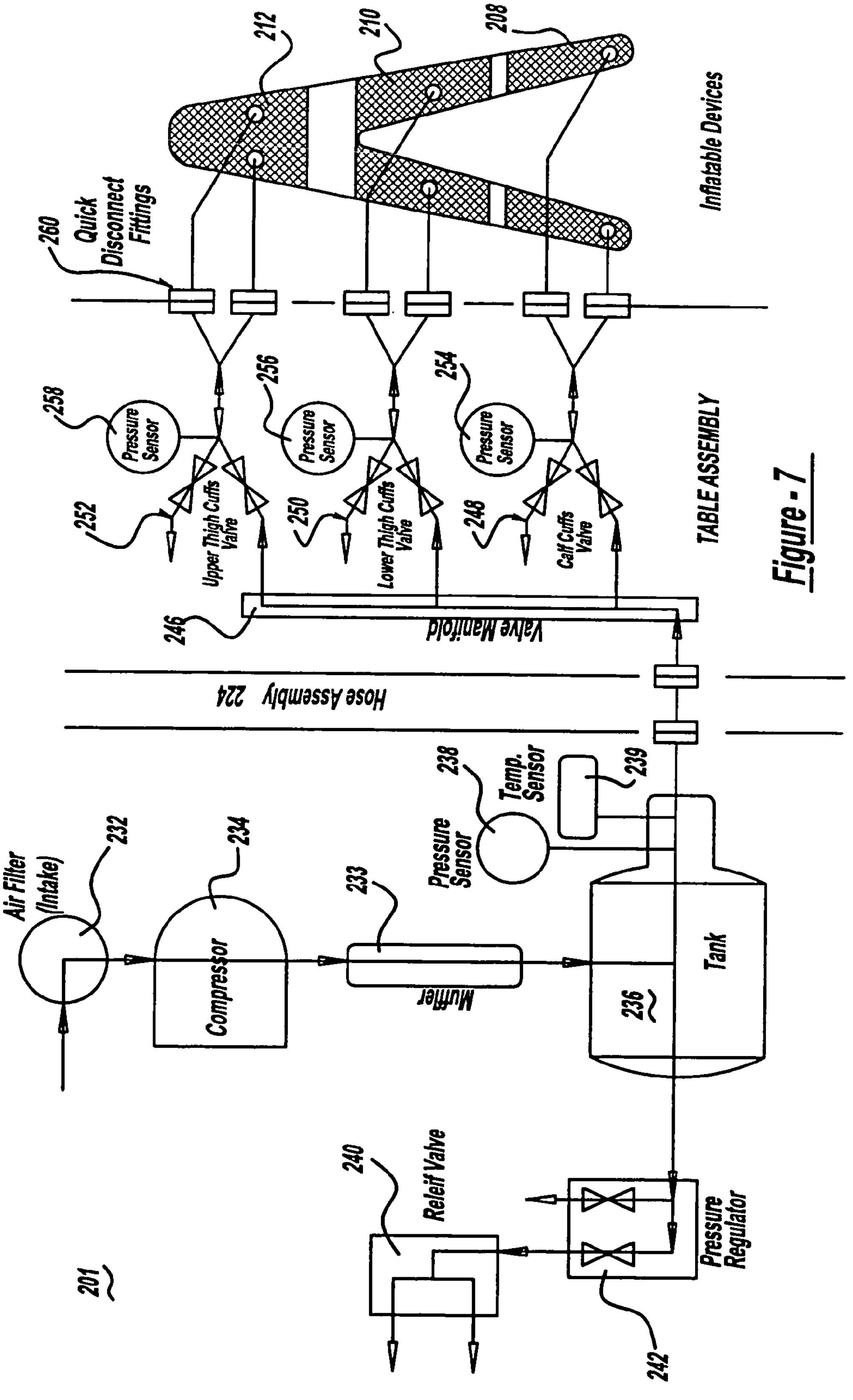
FIG. 7 is another flow diagram of fluid flow of the external counterpulsation apparatus according to the present invention.

FIGS. 6 and 7 are schematic or diagrammatic representations of the compressed gas flow arrangement for the external counterpulsation apparatus 201 generally including the control console 202, treatment table 204, and inflation/deflation assembly 206. The control console 202 preferably includes an air intake/filter assembly 232, a muffler 233, which can be located before or after a compressor 234 (as shown in contrast in FIGS. 6 and 7), a tank 236, a pressure sensor 238, a pressure relief valve 240, and a pressure regulator 242. The pressure sensor 238 is preferably a pressure transducer, but can be any pressure or temperature sensoring device. A temperature sensor 239 may also be included, as shown in FIG. 7.

A hose connection assembly 244 is used for quick connecting and disconnecting the above-described components with those mounted on, or otherwise associated with, the treatment table assembly 204. Such treatment table assembly components include a valve manifold 246, as shown in FIG. 7, a number of inflation/deflation valves 248, 250 and 252, each with an associated pressure transducer/sensor 254, 256, and 258, respectively. A connect/disconnect assembly 260 is provided for quick and easy connection and disconnection of the inflation/deflation valves 248, 250 and 252 with their associated inflatable devices 208, 210, and 212, respectively, of the inflation/deflation assembly 206.

Figure 8:
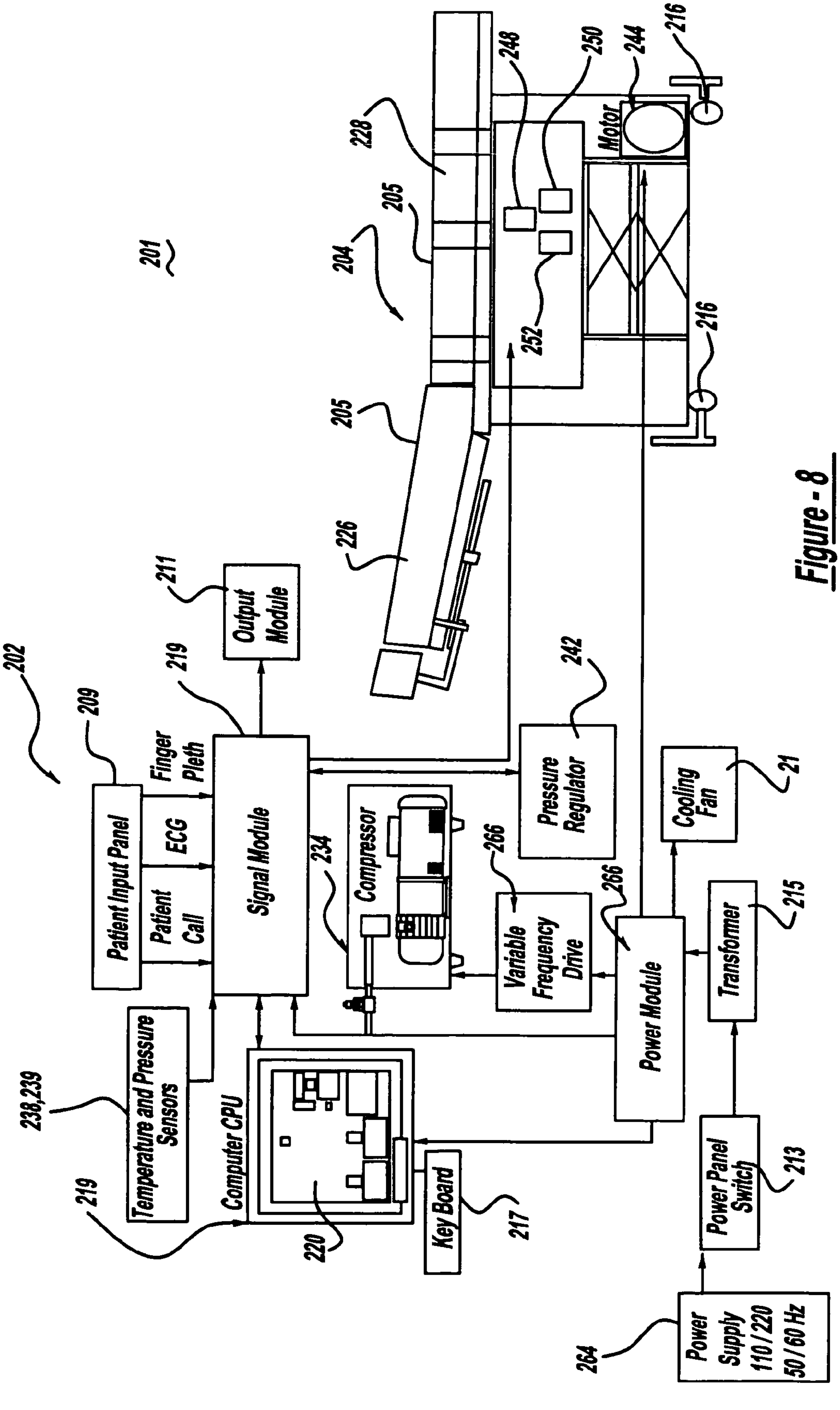
FIG. 8 is a control diagram for the external counterpulsation apparatus of FIGS. 5 through 7.

FIG. 8 diagrammatically illustrates the electrical/logic/control interconnections of the various components of the external counterpulsation apparatus 201. The control console assembly 202 includes a power supply 264 that feeds power to a computer assembly 219, which includes a CPU and the user interface monitor 220, as well as other input provisions such as a keyboard and touch screen; as well as to the compressor 234, by way of a power switch panel 213, transformer 215, and power module 266, which includes a power converter and ramp-up assembly. The power module 266 converts electrical power to the compressor from 110/120 VAC 50/60 Hz to three-phase 220 VAC at a variable frequency and increases the electrical power to a preselected full power level over a period preferably of approximately three (3) to approximately five (5) seconds. At the onset of external counterpulsation treatment for the patient, electrical power is required to power the three sets of inflation/deflation valves 248, 250, 252, as well as to provide the base line requirement of electrical energy to the computer 219, the user interface monitor 220, and other electronics associated with the external counterpulsation apparatus 201. This can result in a power surge of up to or even exceeding 30 amperes. This power requirement is too high for most normal house power supply systems. Therefore, the power module 266 includes a variable frequency drive transistorized inverter (e.g., Mitsubishi Model FR-E520-1.5K) to slowly ramp up the power supply to the compressor 234 over the above-mentioned preferred period of approximately three (3) to five (5) seconds. The power module 266 converts 110/220 VAC 50/60 Hz line input and converts it to three-phase 220 VAC and with variable frequencies, starting at zero (0) Hz and up to a preset frequency (e.g., 72 Hz). Thus, the operation of the compressor 234 is independent of the input line's frequency, and there is no sudden power surge required to start the compressor 234.

In terms of user friendliness, various related functions of the system 201 are grouped for easy and logical operation. All patient-related inputs (patient ECG, finger plethysmography, patient call button, etc.) are located in one location, namely on a patient input panel 209 associated with the treatment table assembly 204. Outputs, such as printer outputs, patient signals, outputs, service signals, outputs, etc., are also grouped in one location, preferably as part of an output module 211 on the control console assembly 202. Operator inputs for purposes of adjusting performance of the apparatus 201, are all on the touch screen display of the user interface monitor 220, and include inflation/deflation timings, magnitude of pressure applied, and other important data discussed below, including the display of the patient's ECG, graphic representations of the inflation/deflation timings, plethysmogram (ear lobe, finger, temporal, etc.) for monitoring appropriate timing adjustment and other operational factors. A keyboard 217 also may be provided. All inputs and outputs are preferably communicated through signal module 219.

Figure 9B:
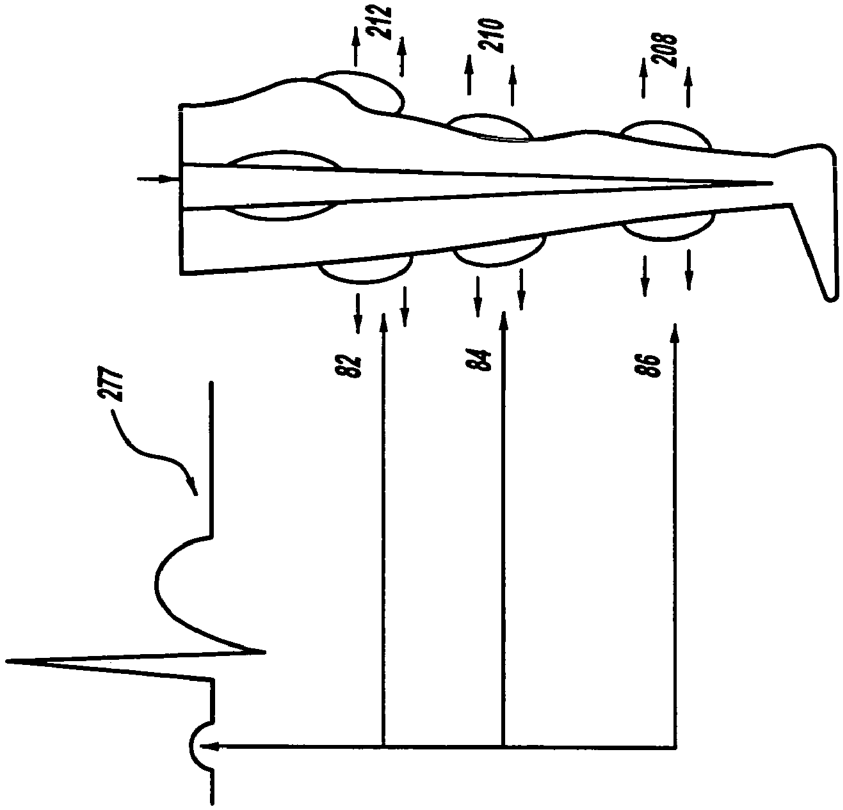
FIGS. 9A and 9B are diagrammatic representations of inflation and deflation of inflatable cuff devices of the present invention, coordinated with the associated portions of the patient's ECG.
Figure 9A:
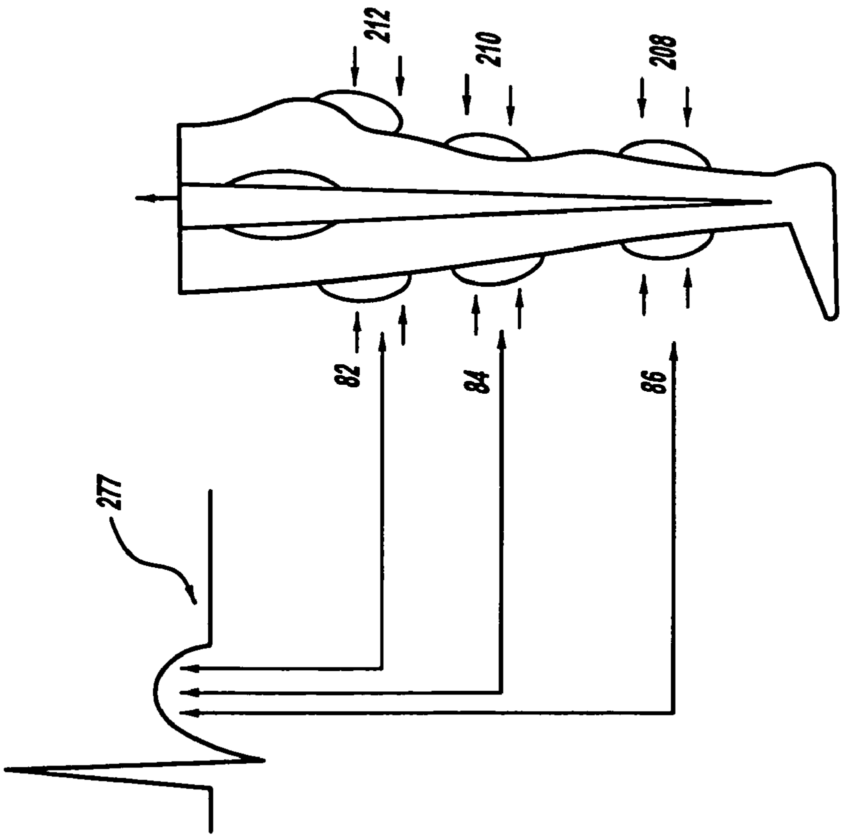
Figure 10:
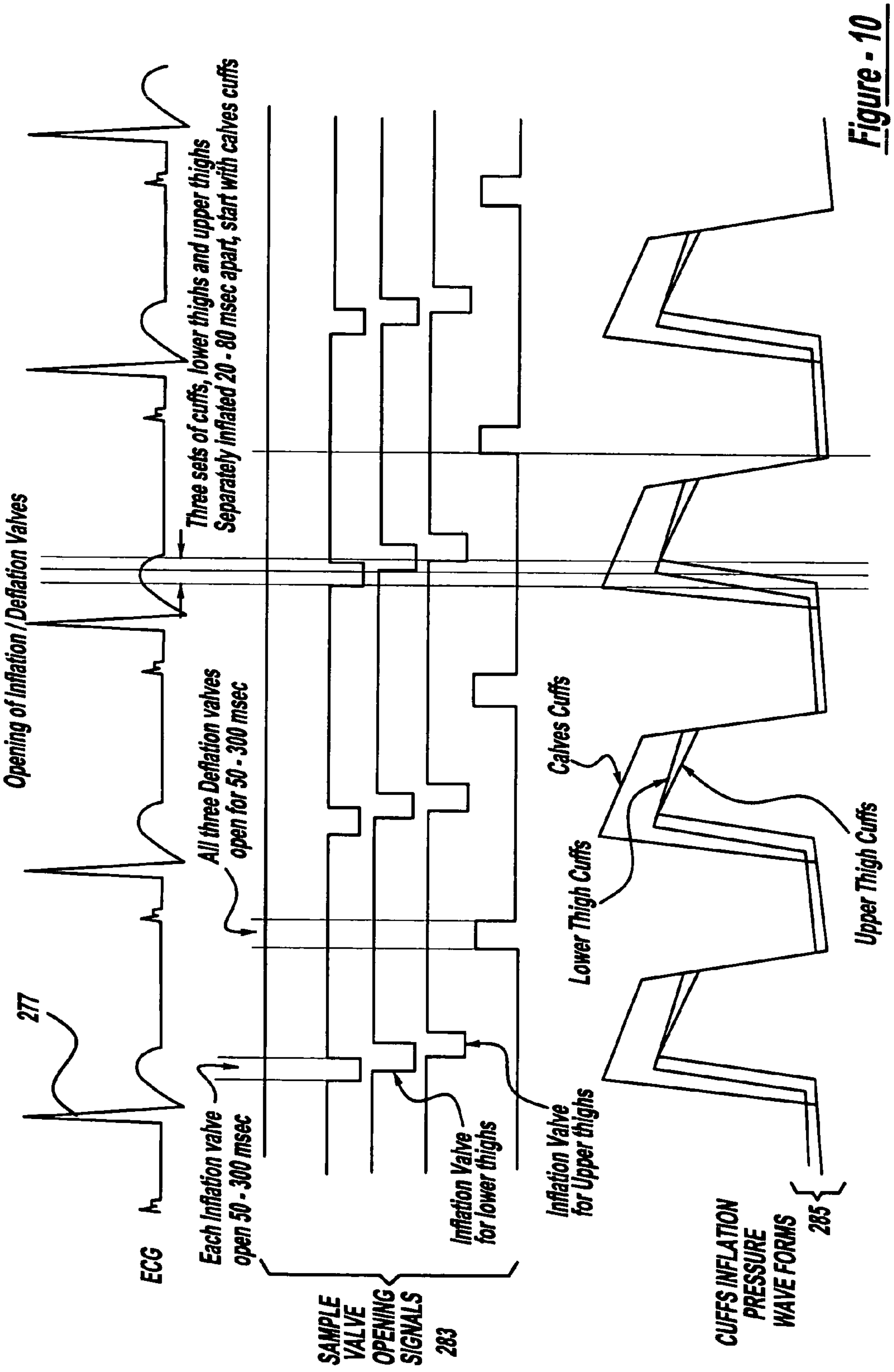
FIG. 10 is a graphic representation of the relationship between the patient's ECG, the valve opening signals and the inflatable cuff device inflation pressure waveforms during operation of the external counterpulsation apparatus of FIGS. 5 through 9.
Figures 11A, 11B:
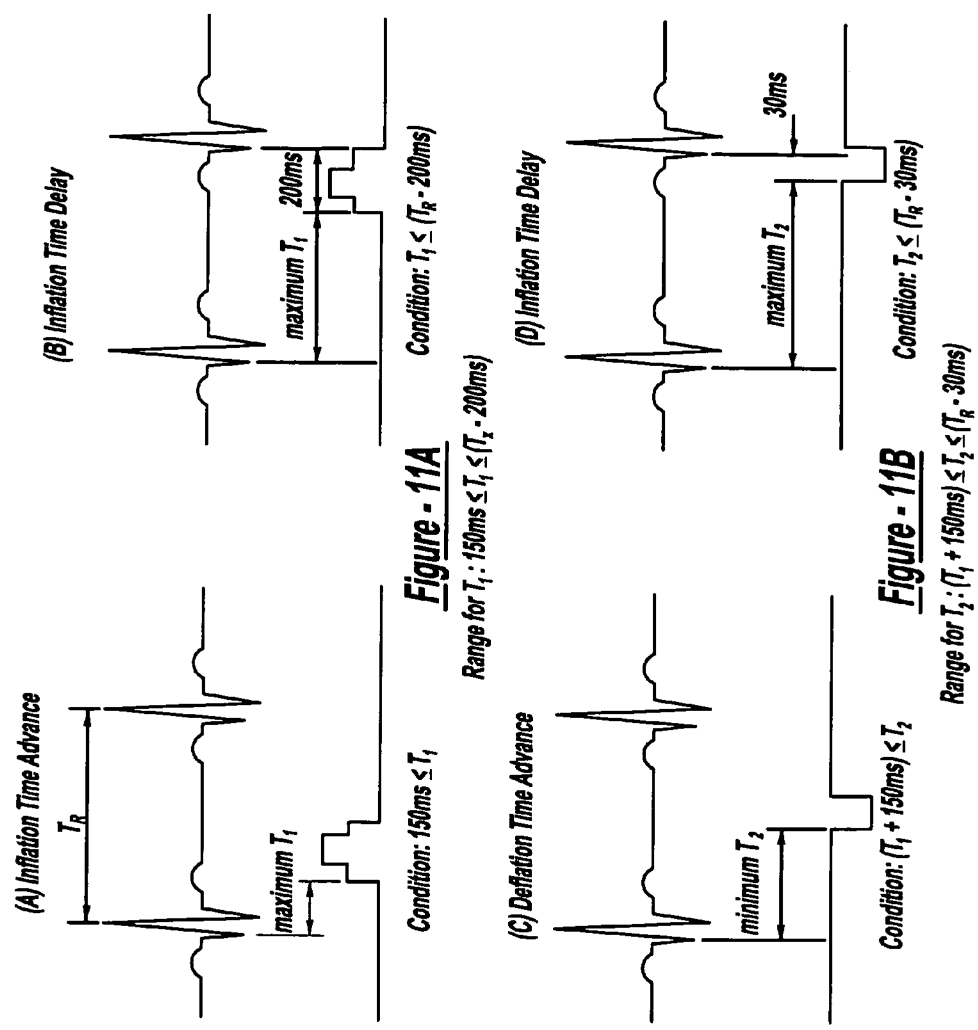
FIGS. 11A and 11B are graphic representations of possible inflation time advances and delays and possible deflation time advances and delays.
Figure 12:
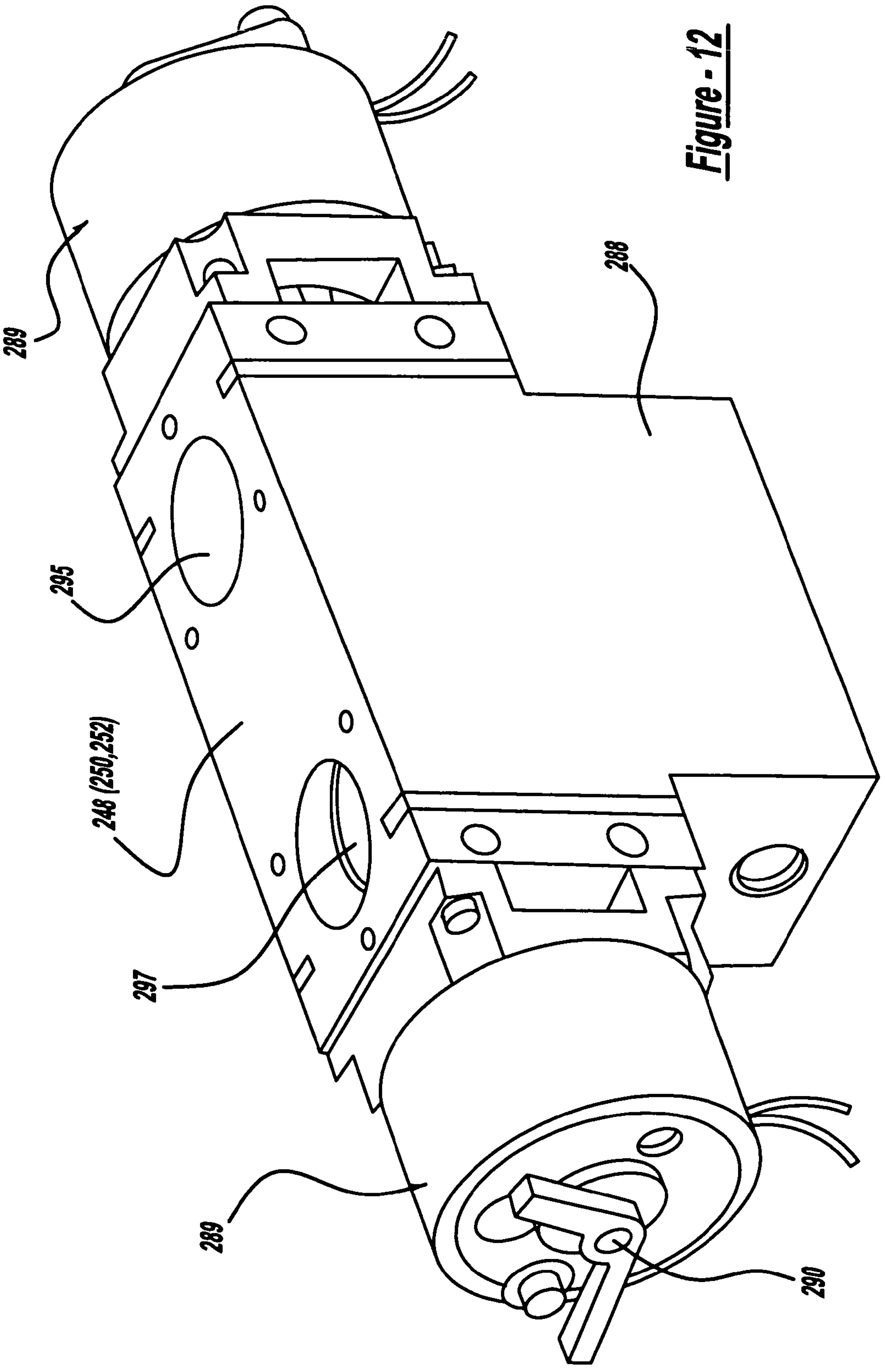
FIGS. 12 through 18 illustrate an exemplary inflation/deflation valve for use in an external counterpulsation apparatus according to the present invention.
Figure 15:
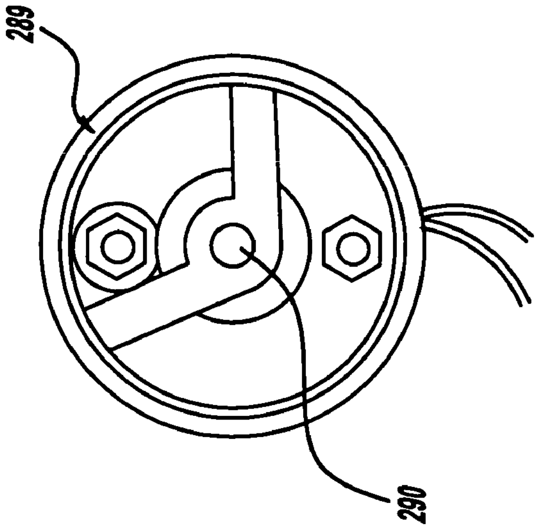
Figure 13:
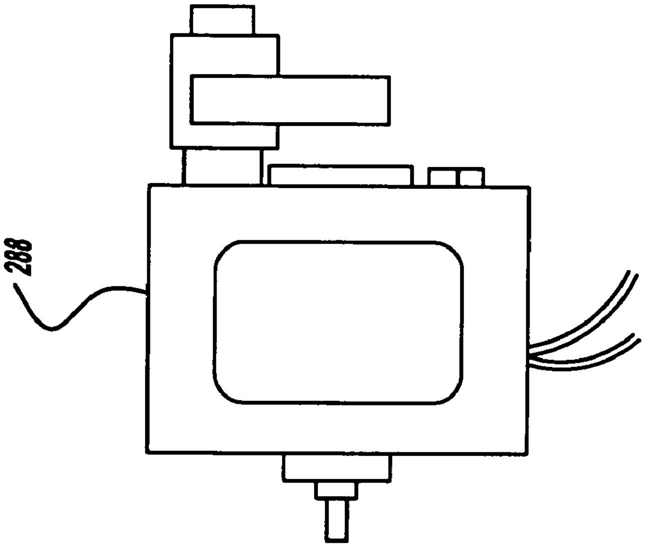
Figure 14:
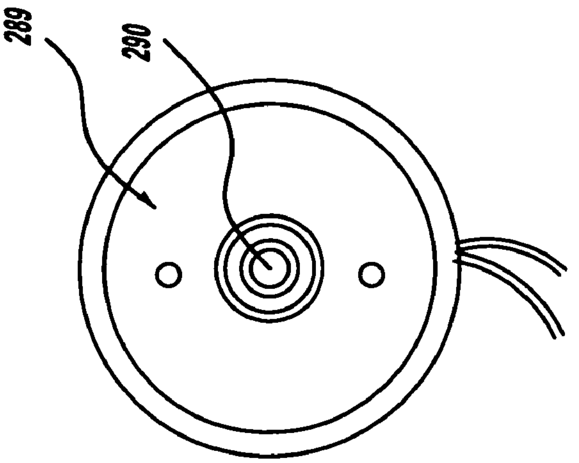
Figure 16:
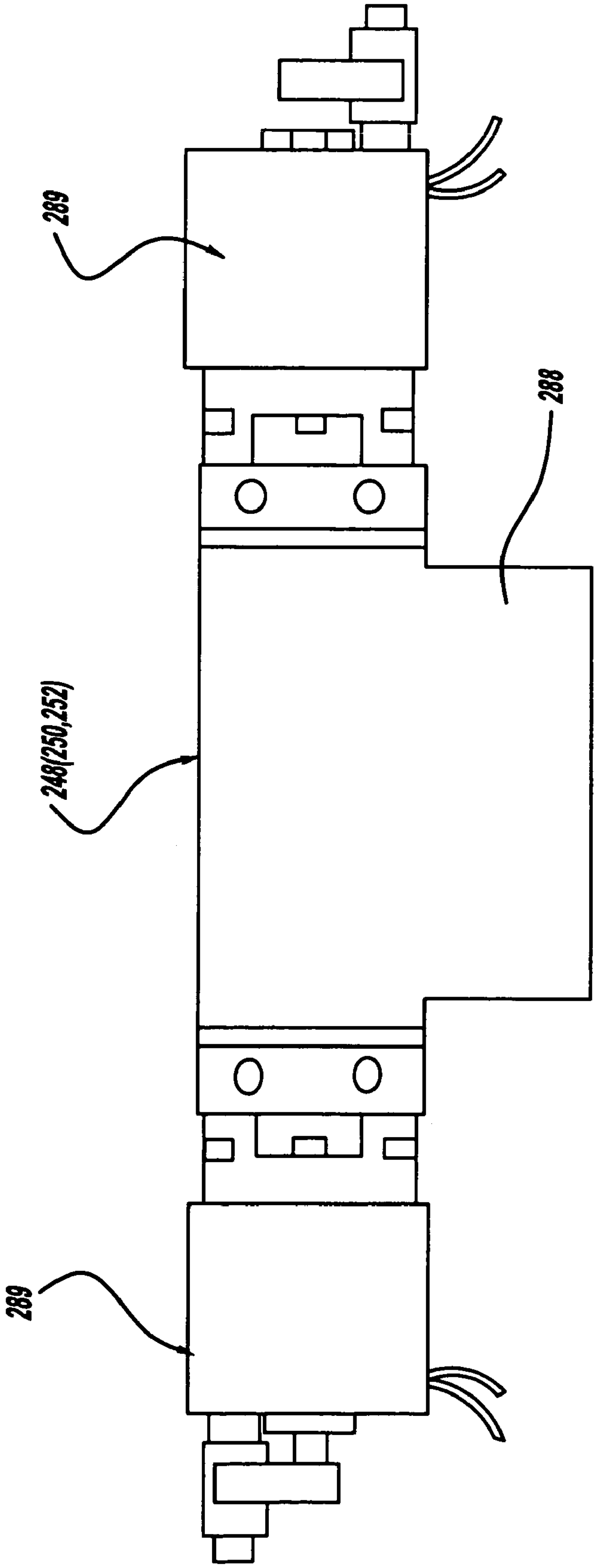
Figure 17:
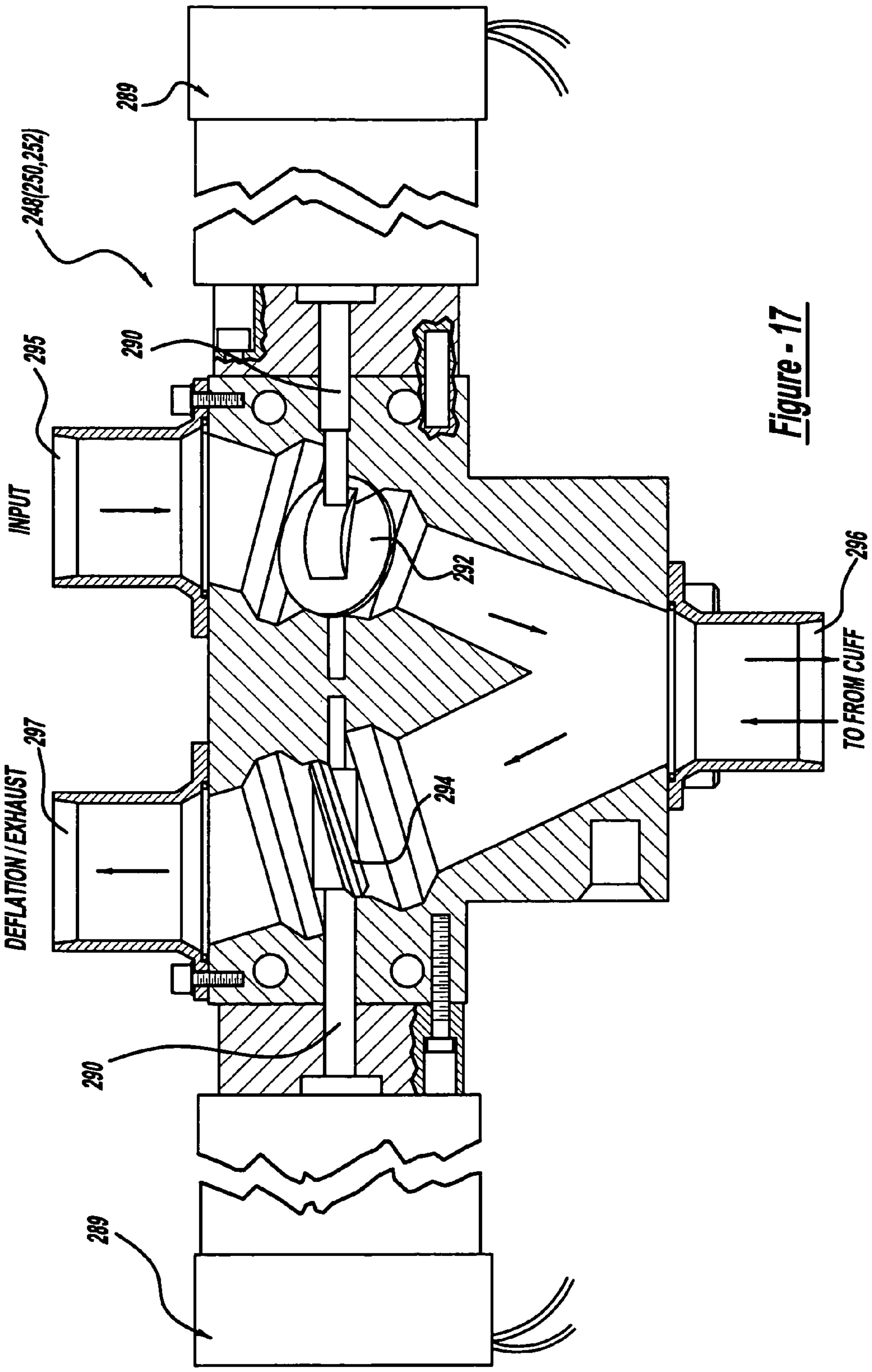
Figure 18:
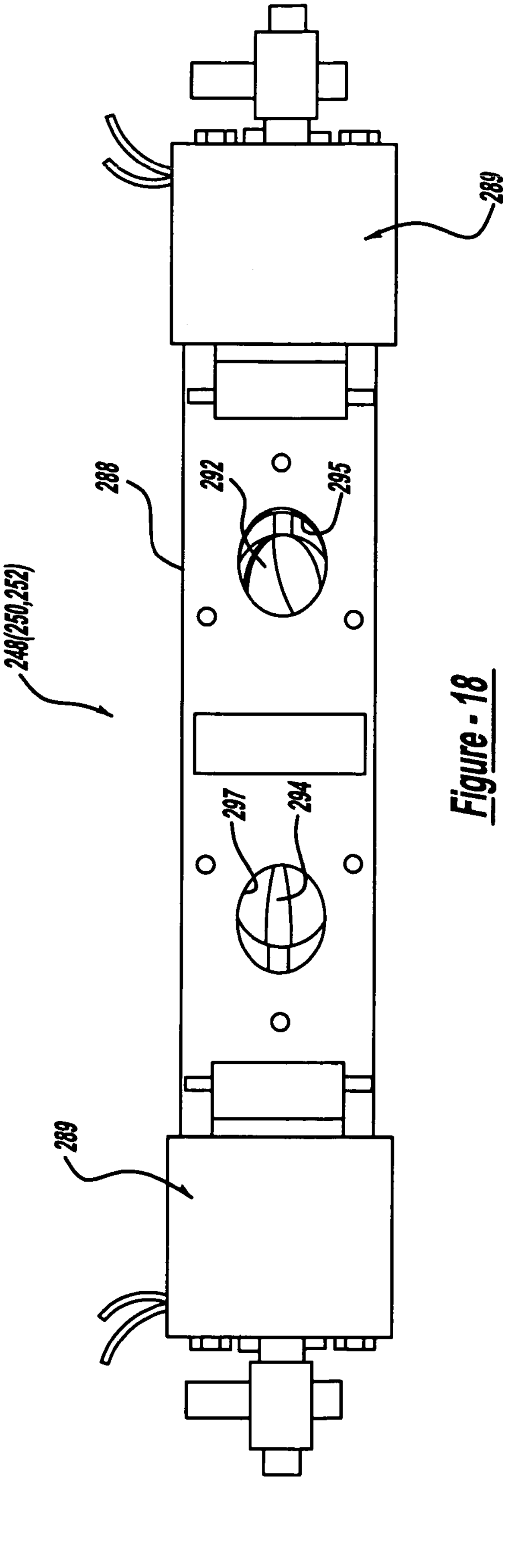

All of the above-described controls and features are configured and calculated to provide for sequential pressurization of the patient's lower limbs, beginning at the most distal area at which the inflatable device 208 is applied, followed by an intermediate area at which the inflatable device 210 is positioned, and ending with the pressurization by the inflatable device 212 at the upper end of the patient's leg or the buttock area. This sequence is indicated graphically in FIGS. 9A and 9B, with the exhausting of all pressure to the inflatable devices 208, 210 and 212 occurring near the end of the ECG cycle, as illustrated in FIG. 9B. This relationship is also graphically illustrated in FIG. 10, which juxtaposes the ECG signal 277, the valve opening signals 283 and the inflatable cuff device pressure waveforms 285. As illustrated in FIGS. 11A and 11B, the inflation time can be advanced or delayed by the operator between certain minimums and maximums.

FIGS. 12 through 18 illustrate an exemplary inflation/deflation valve 248, which should be regarded as typical for the inflation/deflation valve 250 and 252 as well. The inflation/deflation valve 248 (and 250 and 252) is preferably a rotary actuable butterfly-type valve, which can be actuated pneumatically or in the preferred embodiment electrically by the respective operators 289 on opposite ends of a body portion 288 for controlling the rotatable rotors 290. Attached to the rotors 290 are butterfly valve elements 292, 294 which open and close the compressed gas or compressed air inlet 295 and the inflation/deflation port 296, which is connected to the respective or associated inflatable cuff devices 208, 210, or 212, with the butterfly valve element 294 being rotatable actuable to open and close fluid communication between the inflation/deflation port 296 and a deflation exhaust port 297. The quick-acting operators 290 are respectively actuated and controlled by way of the control system described herein, in order to provide for proper inflation and deflation timing and sequential operation of the inflatable devices 208, 210, 212. The butterfly valve elements 292, 294 and their associated rotors 290 are preferably rotatable through a maximum rotation angle of approximately 60 degrees between open and closed positions. A larger or smaller rotation angle is within the scope of the invention.

The inflation passageway through each of the butterfly valve openings between the input port 295 and the inflation/deflation port 296 is more restricted than the deflation passageway between the inflation/deflation port 296 and the deflation exhaust port 297, with the restriction being approximately twenty (20) to thirty (30) percent larger on the deflation side than on the inflation side in order to allow deflation of the inflatable devices 208, 210, 212 at the same rate as the inflation rate, owing to the fact that the inflation has a higher pressure gradient between the compressed gas at the input 295 and the inflation/deflation port 296 when compared with the pressure gradient between the inflation port 296 and the deflation exhaust port 297.

The butterfly valve elements 292, 294, along with their associated rotors 290 are driven by a rotary solenoid using fifteen (15) volt DC continuous power or twenty-seven (27) volt DC, fifty milliseconds pulse, dropping back to a fifteen (15) volt holding voltage. This lower power consumption is important not only, to reduce the overall electrical power requirement, but to reduce the heat output.

For safety and other quick-acting purposes, the deflation butterfly valve element 294 is normally open (such as in a power-off condition) and the inflation butterfly valve element 292 is normally closed. Thus, in the case of a power loss, the inflation valve element 292 will be closed and the deflation valve element 294 will open to allow air from the inflatable cuff devices to deflate and exhaust to atmospheric pressure.

Each of the butterfly valve elements 292 and 294 can be opened from approximately fifty (50) to three hundred (300) milliseconds, and are preferably open from one hundred (100) milliseconds to two hundred (200) milliseconds, to allow compressed air from the above-mentioned reservoir to be admitted to the inflatable devices during the onset of a diastole. As mentioned above, the timing and opening times of the inflation valves are variable in order to correctly correspond with the patient's heart rate, but preferably not less than approximately one hundred (100) milliseconds duration. At the end of a diastole, the deflation butterfly valve element 294 opens (even without electrical power) for a period of approximately fifty (50) to three hundred (300) milliseconds and preferably one hundred twenty (120) to two hundred twenty (220) milliseconds. It is desirable to make the period of opening of the deflation butterfly valve element 294 variable according to the heart rate, but with an opening time of not less than approximately one hundred twenty (120) milliseconds during normal operation. It should be noted that it would be possible to use three-way valves, as discussed above. It is important, however, to prevent cross-overleakage if such three-way valves are used when switching from the inflation port to the deflation port and vice versa.

Figure 19:
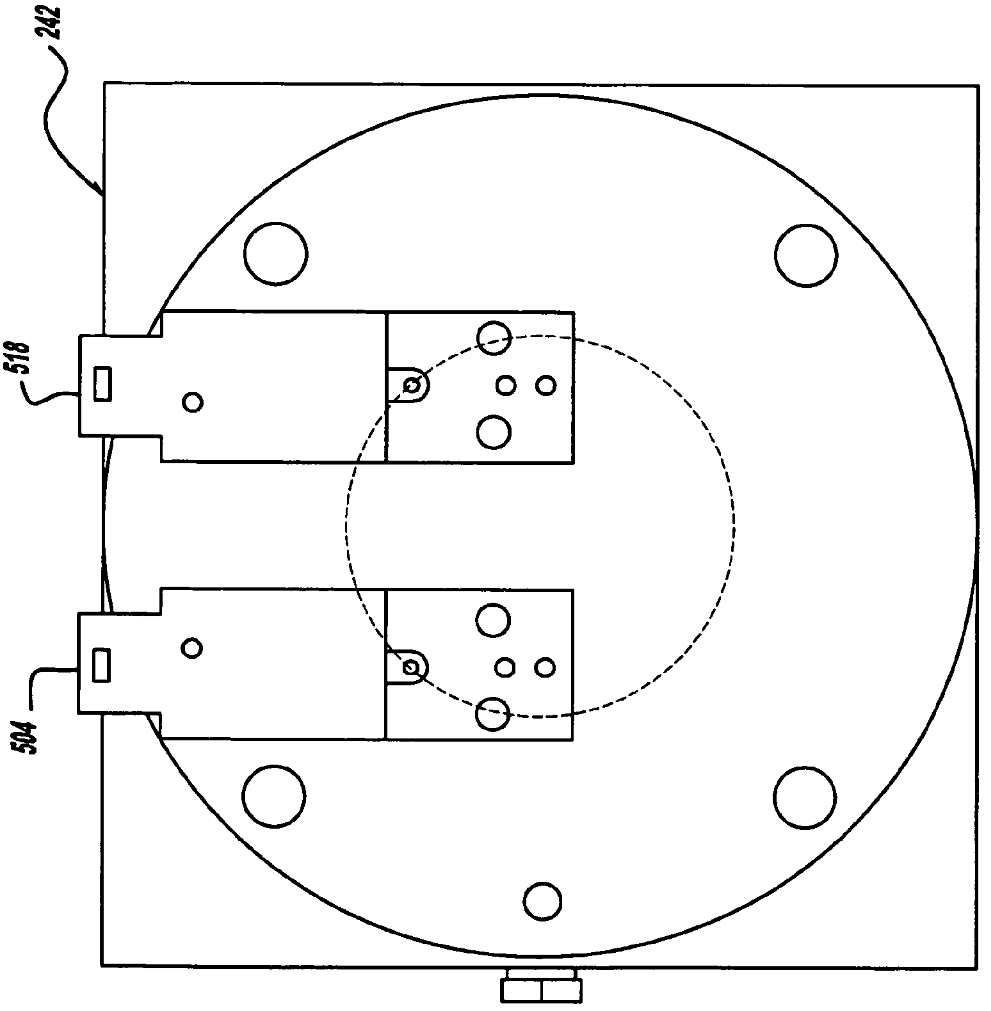
FIGS. 19 through 22 illustrate a pressure regulator assembly for use in an external counterpulsation apparatus according to the present invention.
Figure 20:
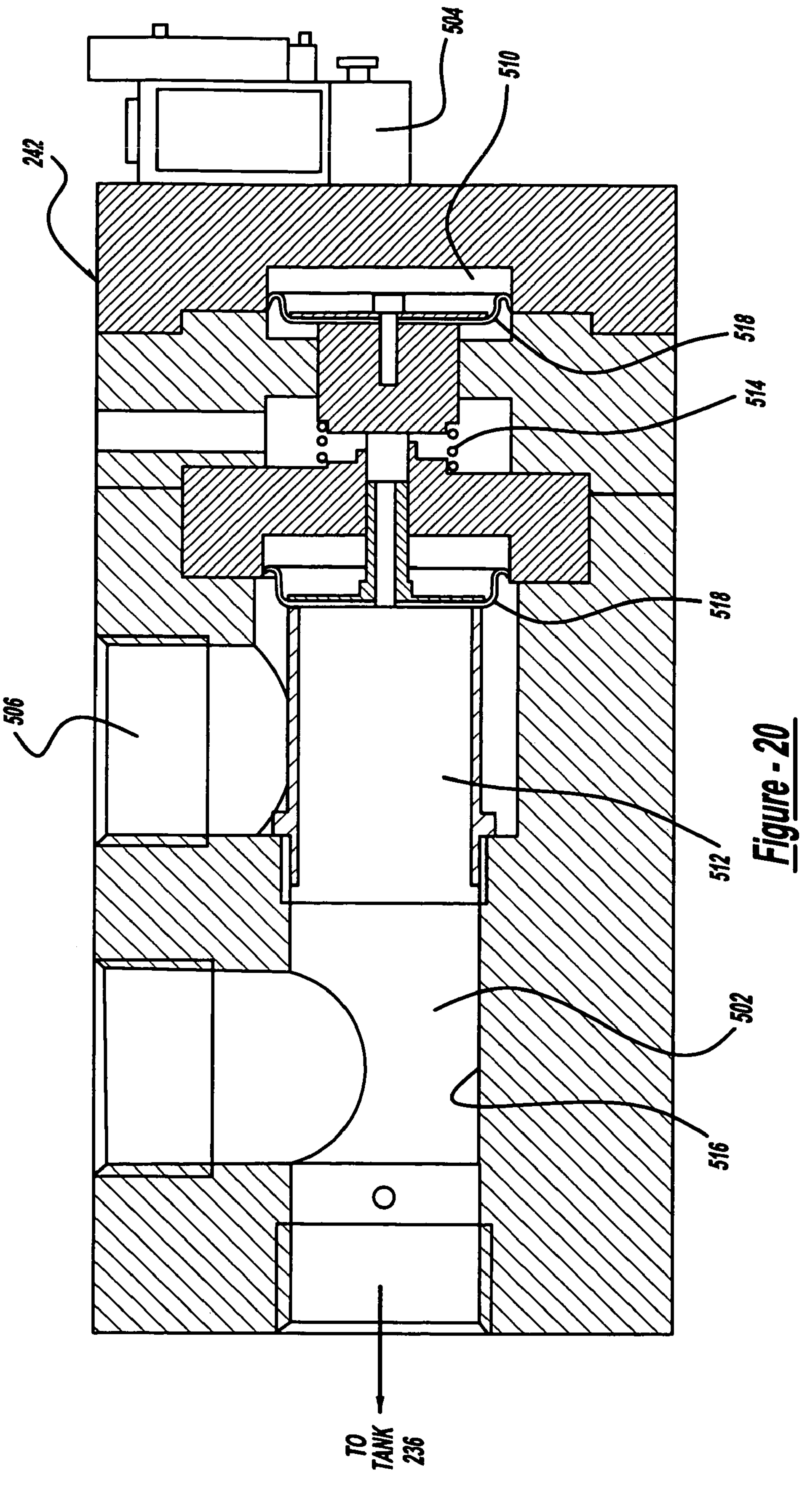
Figure 21:
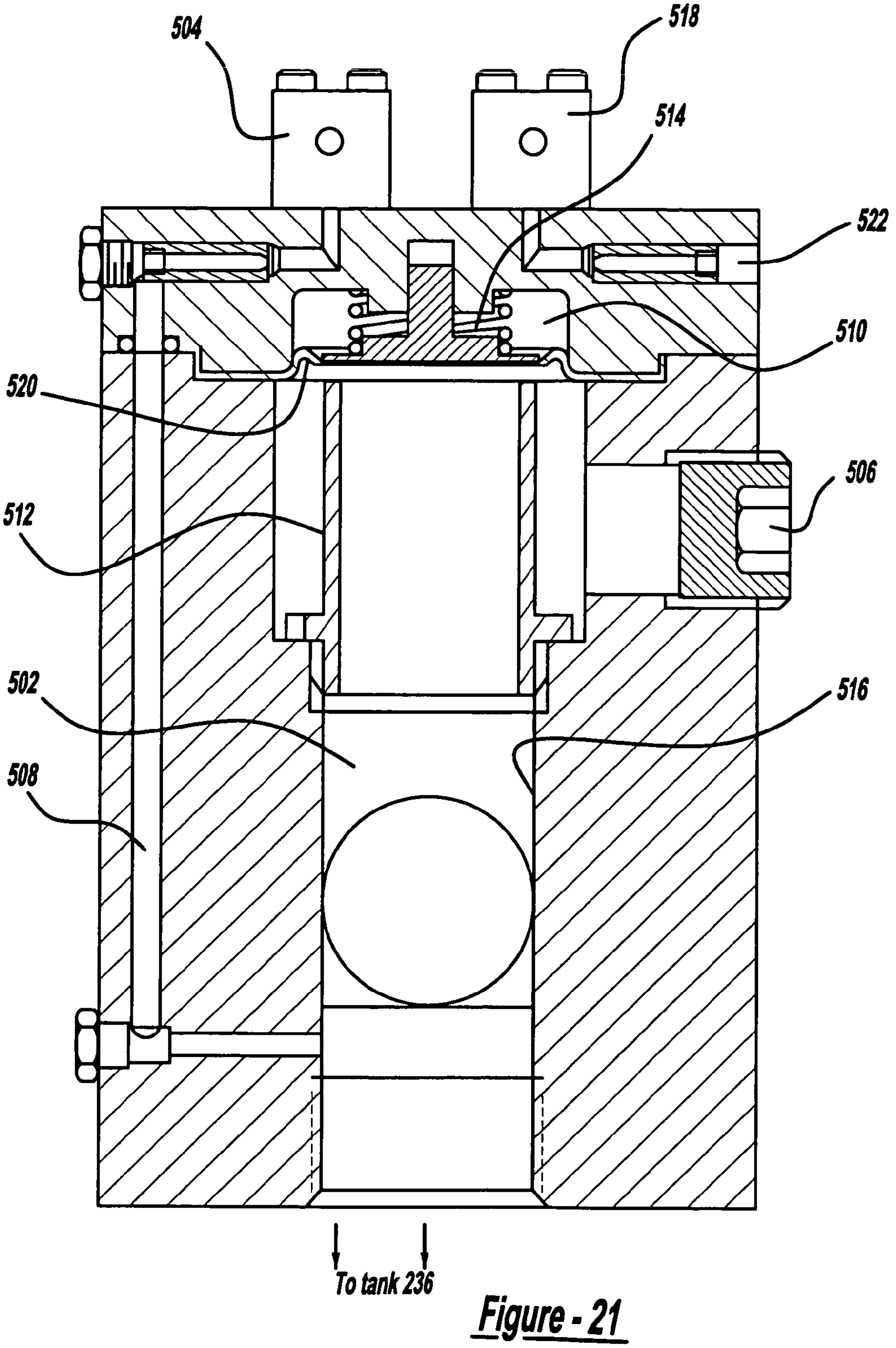
Figure 23:
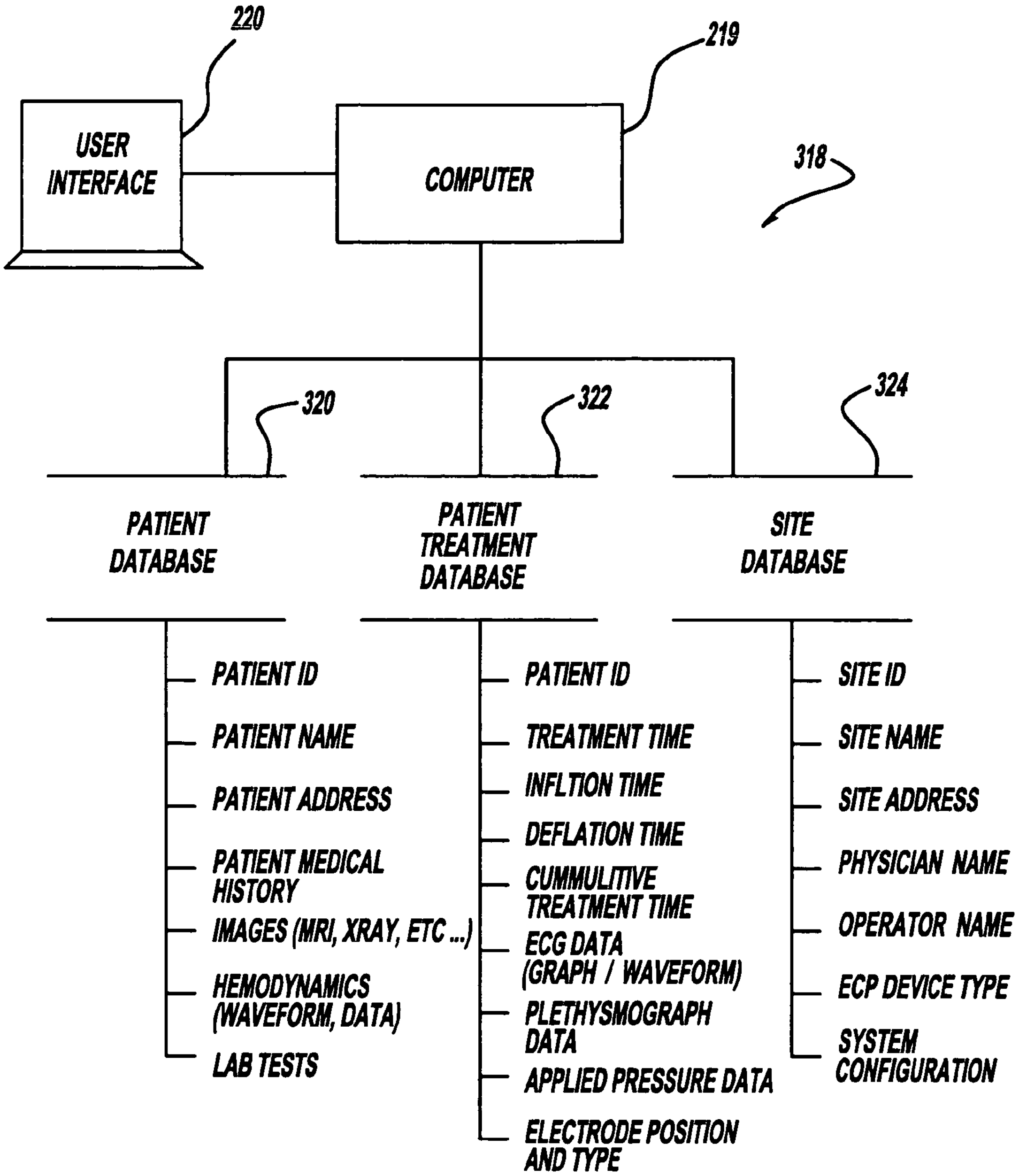
FIG. 23 is a block diagram depicting a computer system for monitoring and recording the treatment of a patient using an external counterpulsation device in accordance with the present invention.
Figure 24:
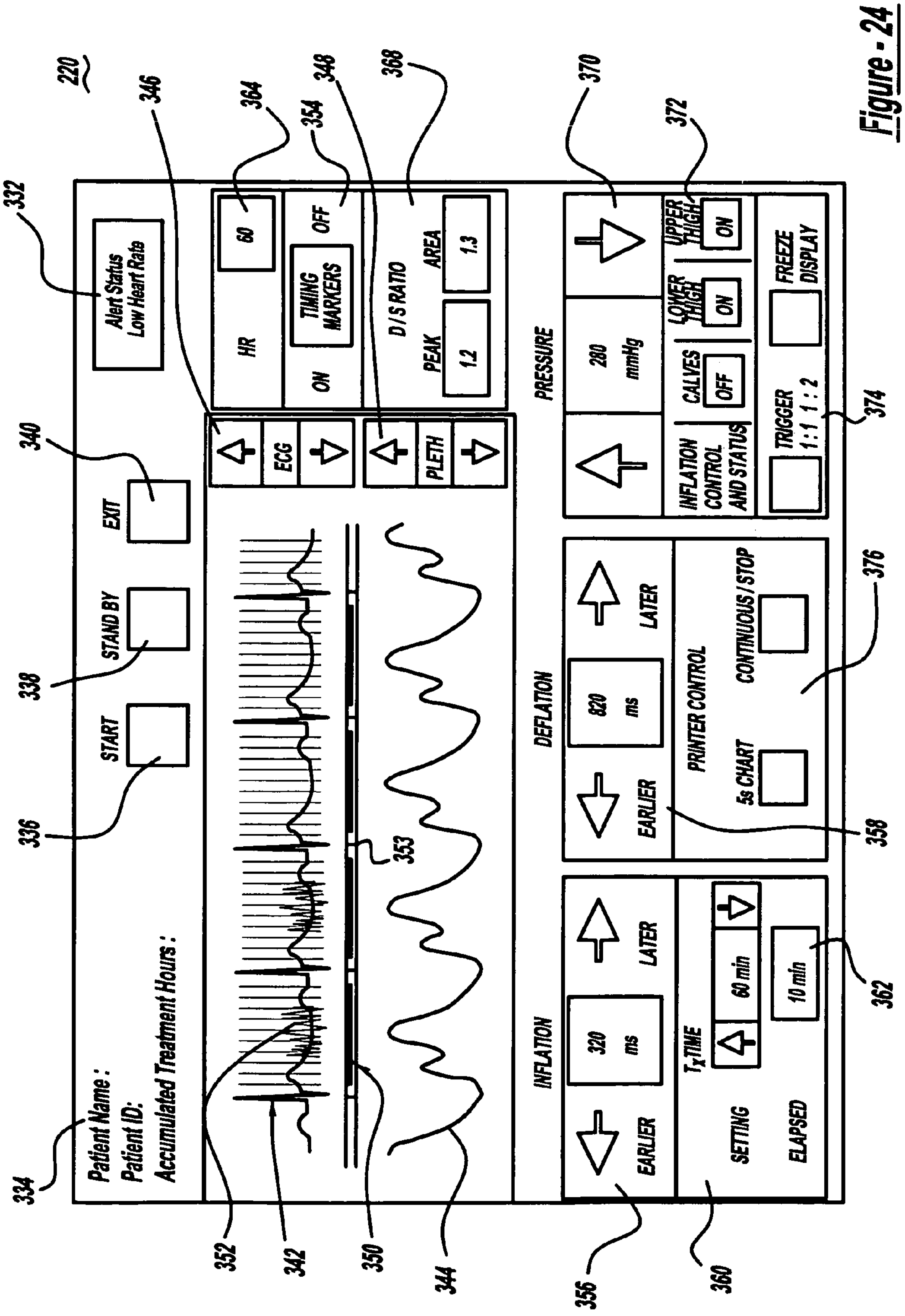
FIG. 24 illustrates an exemplary treatment control screen for the enhanced computer system of the present invention.

As illustrated in FIGS. 19 and 20, the exemplary pressure regulator assembly 242 is a proportional-control pressure-relief valve, preferably providing for an adjustment range of approximately one (1) to approximately ten (10) psi for the tank 236 discussed above. Upon startup of the external counterpulsation apparatus 201, a pressure regulation chamber 502 is vented to atmosphere. Once the compressor comes on and begins to pressurize the tank 236, a control or load valve 504 of the pressure regulator assembly 242 remains open to an exhaust port 506, providing for minimum tank pressure built-up. The flow of fluid to the pressure control chamber is controlled by the load valve 504. When the load valve 504 is energized, compressed fluid will flow through a pathway 508 connecting the pressure regulation chamber 502 to a pressure control chamber 510. As shown in FIG. 23, the pressure control chamber 510 and pressure regulation chamber 502 are separated by a pair of diaphragms 518. As long as the pressure in the pressure regulation chamber 502 is lower than the pressure in the pressure control chamber 510, there is no fluid leak through the pressure exhaust port 506. When the operator-selected pressure is reached, the load valve 504 is closed, pressure continues to build up in the reservoir and the pressure regulation chamber 502 will push a reservoir control piston 512 against the bias of spring 514, opening the exhaust port 506 and leak the build-up pressure to atmosphere. When the pressure drops to the operator-selected pressure, i.e., the pressure in the pressure control chamber 510, the reservoir control piston 512 will move back into cylinder 516, closing the pressure exhaust port 506. When the operator wants to lower the selected pressure, a bleed valve 518 is opened, leaking fluid from the pressure control chamber 510, lowering its pressure, and the reservoir control piston 512 will again move against the bias of spring 514, exposing the pressure regulation chamber 502 to the atmosphere through the exhaust port 506, and thereby lowering the pressure in the pressure regulation chamber 502. The bleed valve 518 is open to atmosphere via port 522. FIG. 24 illustrates a similar embodiment, differing chiefly in that a single diaphragm 520 separates the control chamber 510 and the pressure regulation chamber 502.

When the rotary solenoid inflation/deflation valves open, a sudden drop in tank 236 pressure occurs. This sudden drop Is sensed by the dome diaphragm which instantly moves down closing the servo vent valve. Immediately, the pressure regulation chamber 502 pressure builds, causing the load valve 504 to close so that the compressor 234 can make up for the sudden tank pressure drop below the desired preset level. If operation of the subsequent inflatable cuff devices causes a drop in the tank pressure, the load valve 504 stays closed so that the tank pressure can recover to the desired preset pressure level in the shortest possible time. When the inflatable cuff devices 208, 210 and 212 are exhausted, the tank pressure recovers quickly due to the fact that the compressor is constantly providing pressurized gas into the tank. When the desired tank pressure set point is reached, the dome diaphragm, sensing the increased tank pressure, moves up, thus opening the pressure exhaust port and reducing the pressure regulation chamber pressure to a value that holds the load valve open at a position that maintains the tank pressure at the desired preset level and exhausts the compressor flow into a muffler and exhaust system.

Preferably the dome control solenoids operate at 24 volt DC 0.6 watts each. The orifice is preferably 0.031 inch in diameter, and the load and bleed valves are two-way two position solenoids, with the bleed valve preferably being a three-way two position solenoid. The load valve is preferably a two-way normally closed solenoid, using 24 volt DC to increase dome pressure. The bleed valve is a two-way normally closed solenoid, using 24 volt DC to decrease dome pressure. A power failure causes the vent port to open and vents the dome pressure, which correspondingly vents the tank pressure.

Figure 22:
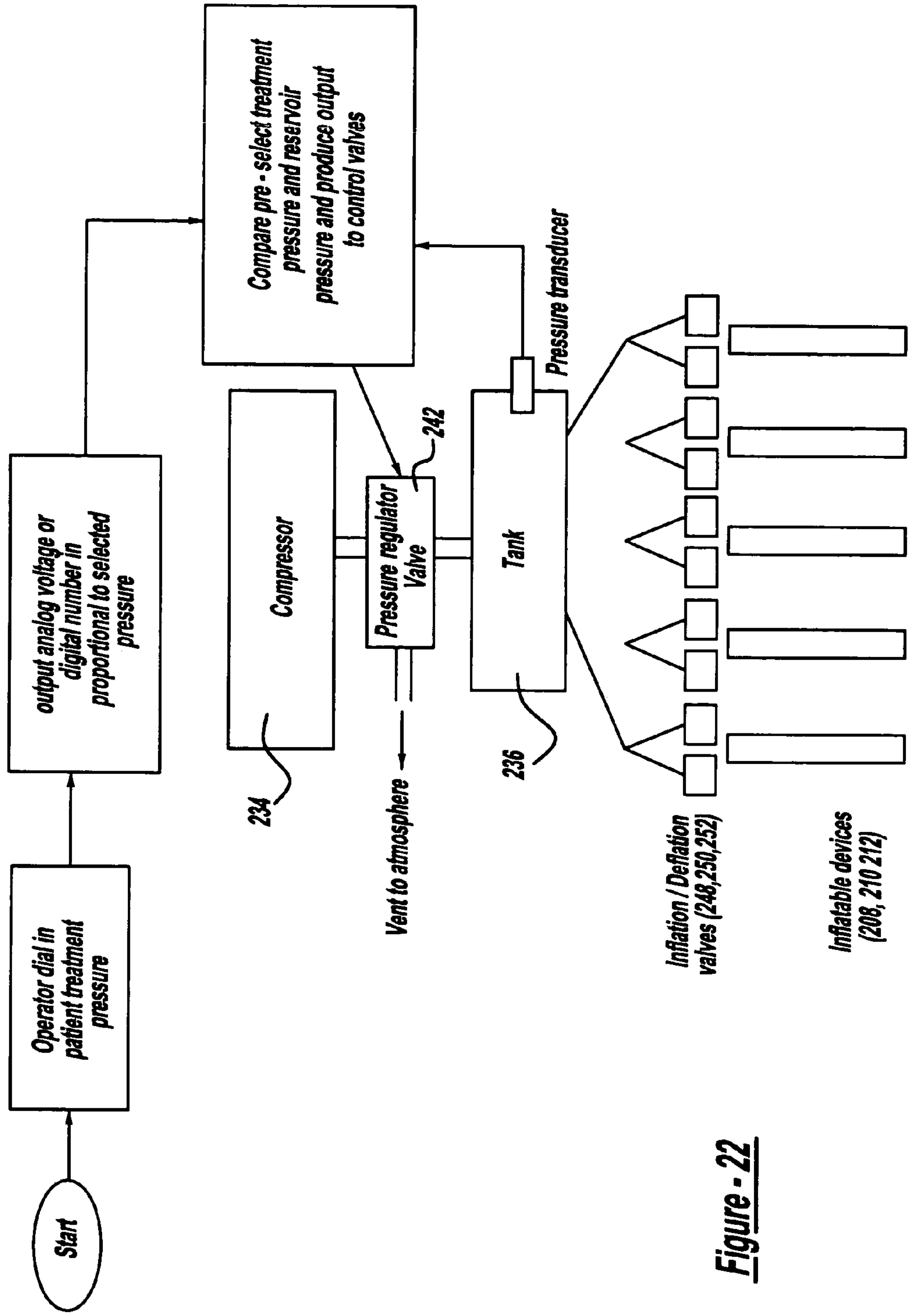

In use, the operator can adjust magnitude of external counterpulsation treatment pressure to be applied to the patient using digital or analog means, as best shown in FIG. 22. The output is either a digital voltage signal or a voltage proportional to the selected pressure. When the operator begins treatment of a patient, the source of compressed fluid, i.e., compressor 234, is activated, sending compressed fluid through a valve, such as a solenoid valve or servo or proportional valve, which is controlled by computer 219. The computer 219 compares the output from the pressure transducer in the reservoir (in analog form and translates to digital form using a analog-to-digital converter) and the operator-selected treatment pressure, and then controls the valve to direct compressed fluid to the reservoir to increase the pressure in the reservoir to the operator-selected level or vent the compressed fluid to atmosphere. When the inflation valve opens, pressure in the reservoir drops and the computer 219 closes the valve to atmosphere and directs compressed fluid to the reservoir to maintain its pressure at or near the operator-selected level. The computer 219 also provides damping means so that the pressure in the reservoir does not run-away in a wild swing to a high or low pressure, but maintains the pressure in the reservoir to within 10-20 mm Hg of the operator-selected level or set point.

FIG. 23 depicts a computer system 318 for monitoring and recording the treatment of a patient who is receiving treatment from the external counterpulsation device of the present invention. As previously described, the computer system 318 is used to control the operations of the external counterpulsation device. The computer system 219 is further operable to monitor and record information associated with the treatment of the patient.

More specifically, the computer system 318 includes a patient database 320 for storing demographic information for one or more patients; a patient treatment database 324 for storing treatment information for one or more patients; a site database 324 for storing information regarding the site of the patient treatment; and the computer 219. For illustration purposes, the computer 219 is a personal computer (PC) having an associated user interface 220, such as a touch screen monitor and keyboard. In this case, the data structures are defined in a storage device associated with the personal computer (e.g., an internal hard drive). More specifically, the data structure for the patient database may include patient identification, such as a number; patient name; patient address; patient medical history, including physician name, disease history, and emergency contact information; image data, such as magnetic resonance images, x-ray images, CAT scan images, etc.; hemodynamic data, such as blood pressure and blood flow information in waveform and data formats; and laboratory test results. The data structure for the patient treatment database may include patient identification; treatment time, such as inflation time, deflation time, and cumulative treatment time; ECG data (in waveform and data formats); plethysmograph data; applied pressure data (for a specific treatment session and cumulative); ECG electrode position; and ECG electrode type. The data structure for the site database may include site identification, such as a number; site name; site address; physician name; device operator name or ID; external counterpulsation device type; and external counterpulsation system configuration.

As is mentioned or described in detail below, the user interface 220 is preferably a touch screen for easy monitoring of patient treatment status, treatment parameters, and other relevant data, and provides the capability for adjustment to control operation. As shown in FIG. 24, the user Interface 220 or touch screen display includes patient data in the upper left hand portion of the display, which is in communication with the patient's data base allowing an operator to create a patient file for each new patient and allowing the system or apparatus 201 to track the accumulated treatment time for proper dosage for the patient.

Ease of initiation and termination of operation is accomplished with three buttons on the top line of the display, namely a start button 336 for initiation and continuation of treatment; a standby button 338 that can be used to place the external counterpulsation apparatus 201 on "hold", whenever the patient needs to rest, use a restroom, or otherwise temporarily pause the treatment, and to then resume when the patient returns to complete the treatment session; and an exit button 340 to stop treatment. The treatment timing function does not run when the standby button is selected, thus allowing it to keep track of total treatment time. The exit button 340 is provided to stop the treatment session for a particular patient and to record the elapsed treatment time in the patient database for use in future treatment sessions.

An ECG display is included with timing markers 352 and bars 350 superimposed on or adjacent the ECG signal 342 for easy identification of inflation and deflation timing, which is illustrated by the graphic inflation/deflation timing markers and bars. The timing markers 352 are amplitude signals superimposed on the ECG signal 342, and should not be misinterpreted as noise. Further, the markers 352 can be turned "on" or "off" for easier identification of the ECG signal 342. The timing bars identify a trigger signal 353, which can be checked against the ECG's R-wave, as well as the inflation and deflation times, which demonstrate the period of the cardiac cycle when external pressure is applied. This enables operators to easily identify and verify that they are not inflating the inflatable devices 208, 210, 212 during the cardiac systole, when the heart is pumping or ejecting blood. The user interface 220 also includes digital display of inflation and deflation time 358, digital display of the magnitude of external pressure applied 370, digital display of the intended treatment period 360. The default treatment period is preferably 60 minutes. Inflation time, deflation time, magnitude of pressure applied, and treatment period can be manually adjusted by the operator. Digital display of the elapsed treatment time is also provided at 362 and the three pairs of inflatable devices can individually be turned "on" or "off" at 372, which condition is easily identified and displayed in the lower right hand of the display screen. Further, the inflatable devices can be triggered on every heartbeat, or every other, at 374. Moreover, control of printer functions is provided at 376, including a five (5) second chart or continuous chart. A freeze-display option is provided at 378, whereby a user can freeze the screen for extended examination.

Figure 25:
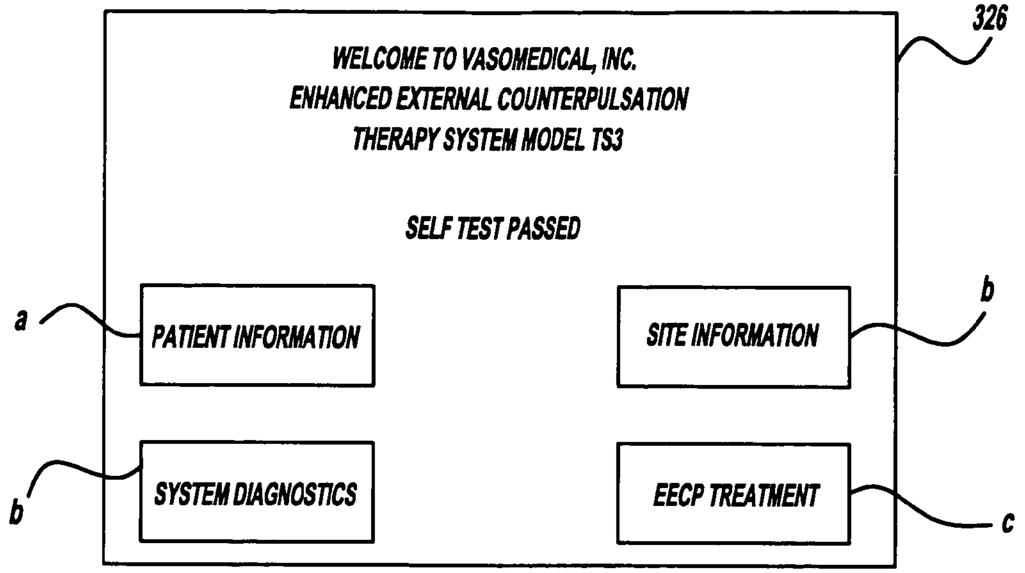
FIG. 25 illustrates an exemplary main menu control screen for the enhanced computer system of the present invention.

FIGS. 24 through 27 illustrate some exemplary control screens that help to better understand the functionality of the enhanced computer system 320. As shown in FIG. 25, a main menu screen 326 allows the operator to select from one of four options: (a) patient information, (b) site information, (c) ECP Treatment, or (d) system diagnostics. The patient information and site information options allow the operator to enter patient information and clinical site information, respectively, into the system. The ECP treatment option allows the operator to monitor and control the treatment of a patient; whereas the system diagnostic option allows the operator to simulate treatment of a patient for purposes of training the operator and/or testing the equipment of the external counterpulsation device.

Figure 26:
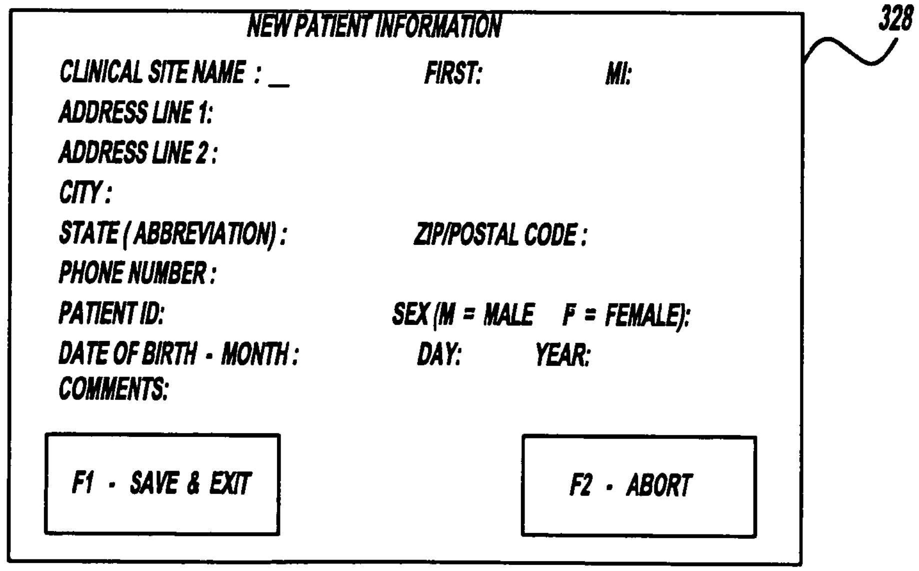
FIG. 26 illustrates an exemplary patient information screen for the enhanced computer system of the present invention.
Figure 27:
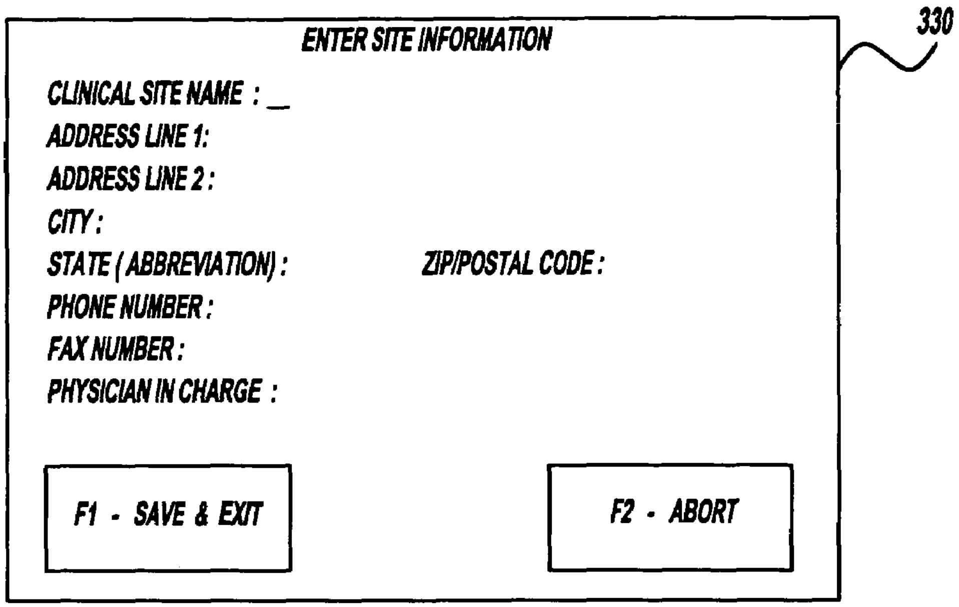
FIG. 27 illustrates an exemplary site information screen for the enhanced computer system of the present invention.

Referring to FIG. 26, the patient information screen 328 permits the operator to input and/or edit demographic information for one or more patients. The patient demographic information may include (but is not limited to) the patient's name, address, phone number, sex, date of birth and other documentation relating to the medical treatment of the patient (e.g., medication, disease history, etc.). Once this information is entered for a new patient, it may be stored into the patient data structure 320. Each new patient may also be assigned a randomly generated patient identification number that is stored in the patient data structure 320.

Figure 28:
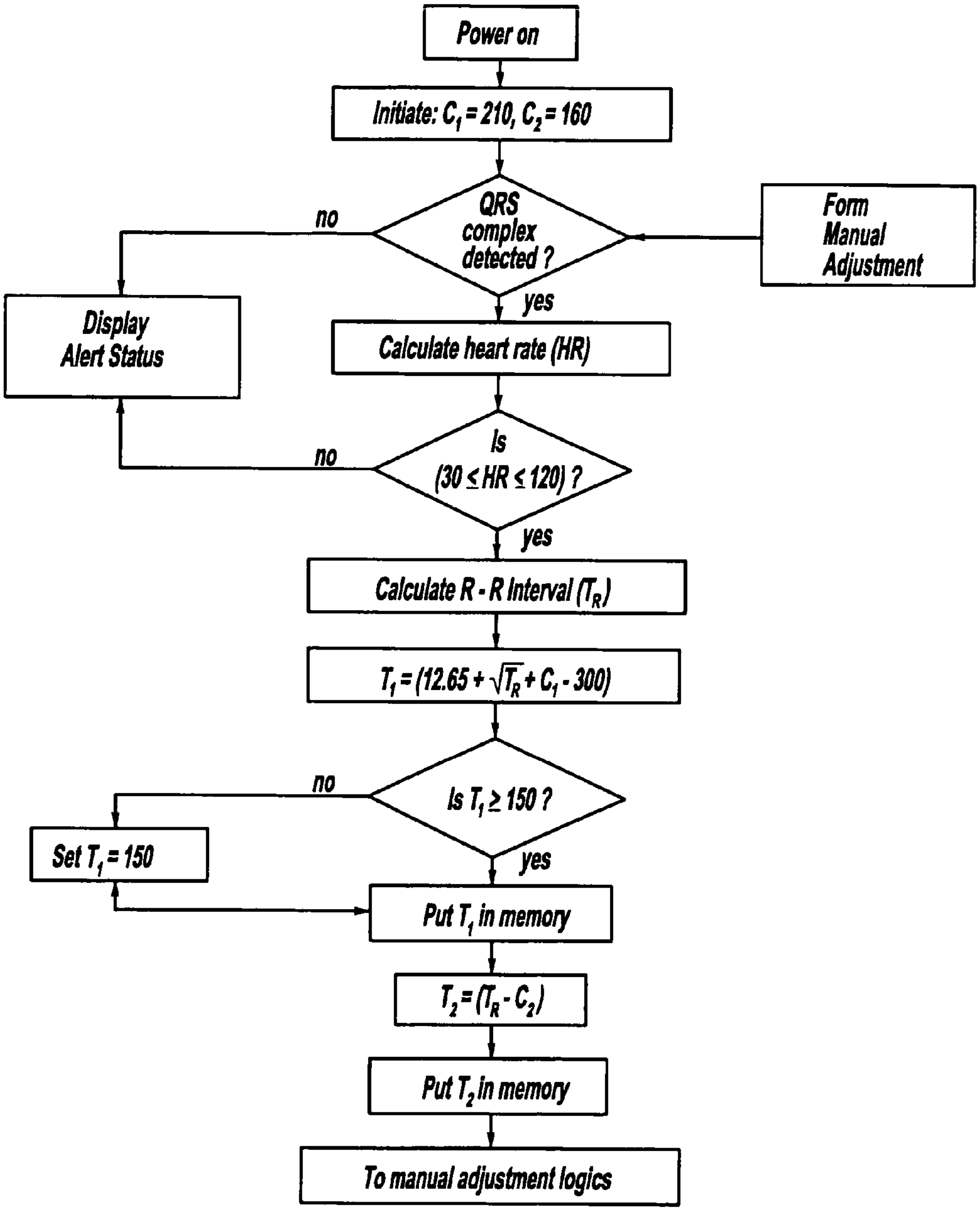
FIG. 28 diagrammatically illustrates initiation timing logics for the inflation/deflation valves of an external counterpulsation apparatus according to the present invention.

Similarly, the site information screen 330 permits the operator to input and/or edit information relating to the clinical site as shown in FIG. 28. The site information may include (but is not limited to) the clinical site's name, address, phone number, facsimile number, and the name of the physician associated with the clinical site. The site information is stored in the site information data structure 324.

FIG. 24, as discussed above, illustrates the primary treatment control screen 332 for monitoring and controlling the patient's treatment as provided by the external counterpulsation device of the present invention. Patient treatment information is prominently displayed in the center of the user interface. The upper waveform 342 is an electrocardiogram (ECG) signal taken from the patient. As will be apparent to one skilled in the art, the R wave portion of the ECG signal is typically used to monitor the cardiac cycle of the patient. The lower waveform 344 is a pressure signal indicative of the blood pressure of the patient. The pressure signal is also used to monitor the cardiac cycle of the patient as well as to monitor the counterpulsation waves being applied to the patient by the external counterpulsation device in a preferred embodiment, the pressure signal is further defined as a plethysmograph waveform signal as received from a finger plethysmograph probe. Two amplitude adjustment switches 346 and 348 are positioned just to the right of each of these waveforms which allow the operator to adjust the resolution at which the signals are viewed.

Timing bars 350 are simultaneously displayed between the upper and lower waveforms. The timing bars 350 indicate when the inflation/deflation cycle is being applied to the patient by the external counterpulsation system. More specifically, the timing signal includes a timing bar for each inflation/deflation cycle, where the leading edge of the timing bar corresponds to the initiation of inflation and the trailing edge of the timing bar corresponds to the initiation of deflation. Further, the timing bars 350 include the trigger signal 353, which indicates the time at which the inflation/deflation cycle is triggered.

The safety and effectiveness of the external counterpulsation therapy depends on the precise timing of the inflation/deflation cycle in relation to the cardiac cycle of the patient. For instance, an arterial wall with significant calcium deposits (hardened artery) will transmit the external pressure pulse up the aorta faster than an elastic vasculature. Therefore, the inflation valves should be opened later for a calcified artery than for a normally elastic artery. Because it is difficult to measure the elasticity of the arterial wall, the operator may have to manually adjust the proper timing of the inflation valves by imposing the requirement that the arrival of the external pulse at the root of the aorta be after the closure of the aortic valves. The enhanced display of the three patient treatment signal enables the operator to more accurately adjust the timing of the inflation valves. This is one exemplary way in which the computer system of the present invention improves the patient treatment provided by the external counterpulsation device.

To further improve the monitoring of the timing of the inflation/deflation cycle in relation to the cardiac cycle of the patient, timing markers 352 may be superimposed over the ECG signal. The timing markers 352 appear for each interval of an QRS wave on the ECG signal. The markers appear as high-frequency noise superimposed on the ECG wave to indicate inflation and deflation in relation to the ORS wave. As will be apparent to one skilled in the art, the amplitude of the signals are adequately sized so that the markers will not be misinterpreted as noise associated with the ECG signal. The timing markers switch 354 allows the operator to turn on/off the display of the timing markers 352 on the screen.

The treatment control screen 332 also provides the switches for adjusting the timing of the inflation/deflation cycle. The inflation adjustment switch 356 allows the operator to adjust the setting of the time for the start of sequential inflation as it is measured relative to the R peak of the ECG signal. Each press of the left arrow causes the inflation to occur some predefined time increment earlier (e.g., ten (10) milliseconds); whereas the right arrow causes the inflation to occur some predefined time increment later. The current setting of the inflation start time is displayed on the middle window of the switch 356. Likewise, the deflation adjustment switch 358 allows the operator to adjust the setting of the time for the start of deflation as it is measured relative to the R peak of the ECG signal. Deflation may be simultaneous or sequential.

In addition, the treatment time for the patient is monitored and controlled by two additional interfaces. The treatment setting switch 360 allows the operator to set the time for the patient treatment. Again, each press of the left arrow causes an increase in the treatment time by some predefined time increment (e.g., one (1) minute) and each press of the down arrow decreases the treatment time by the same predefined time increment. The current setting of the treatment time is displayed on the middle window of the switch 360. An elapsed treatment time display 362 shows the elapsed time of the current treatment session.

Other patient treatment information may also be displayed and/or adjusted through the use of the treatment control screen 332. For instance, a heart rate display 364 may show the heart rate of the patient and a diastolic/systolic ratio display 368 may show the peak ratio and the area ratio of the plethysmograph signal. These displays may be updated periodically, such as upon freezing the display or polling every predefined time period, or may be updated in real time. Additionally, a pressure adjustment switch 370 may be provided to allow the operator to adjust the inflation pressure of the compressed air. It is envisioned that other patient treatment information may be displayed and/or adjusted through various user interfaces as provided on the treatment control screen 332.

FIG. 28 is a block diagram or flow chart summarizing the procedures of the initiation operation and the automatic set up of the inflation/deflation logic for the external counterpulsation apparatus 201. The opening of the inflation/deflation valves are performed by a power switch circuit which reads the values of T1 and T2 from memory. Even though the inflation time T1 appears to be relatively short, i.e., less than one-half of the R-R interval, it represents the time at which the inflation signal is being sent to the power switching circuit to initiate opening of the inflation valves. It takes approximately twenty (20) milliseconds for the valves to fully open, approximately another thirty (30) milliseconds for the air pressure to arrive at the inflatable devices 208, 210, 212, approximately another seventy (70) milliseconds to reach full inflation pressure, and approximately an additional two hundred (200) to three hundred (300) milliseconds for the applied pressure wave to travel from the peripheral vasculature of the legs and thighs to the root of the aorta. By that time, the systolic period would have already passed. For example, take a heart rate of sixty (60) beats per minute, the systolic time is approximately four hundred (400) to five hundred (500) milliseconds per beat. Therefore, for the applied pulse wave to arrive at the root of the aorta at the time the aortic valve closes, the inflation signal should start at about one hundred fifty (150) to two hundred (200) milliseconds after the R wave. In addition, it can be shown that the deflation time happens approximately one hundred sixty (160) milliseconds before the next R wave. Deflation valves for the lower leg and thigh cuffs open to the atmosphere for a duration of one hundred twenty (120) milliseconds. Because the decay time T4 is eighty (80) milliseconds at the most for the inflatable device pressure to drop to zero (0), there is no residual pressure existing in the cuffs at the beginning of the next systolic phase, giving the peripheral vascular bed ample time to refill during cardiac systole.

During the operation stage following the initiation stage, the values of T1 and T2 will be stored in memory and used to control the inflation/deflation timing. However, the memory will be updated with every new heartbeat using the updated TR to calculate the new T1 and T2 and stored in memory replacing the old T1 and T2. In addition, the CPU will interrogate every ten (10) milliseconds a flag in one of the registers to determine if any of the manual adjustment buttons have been pushed. The inflation/deflation adjustment buttons 356, 358 are located on the front panel (screen) for advancing or retarding the inflation or deflation times.

Each depression of the inflation advance button will trigger the CPU to compare the vale (TR-T1) to 200 ms. If (TR-T1) is larger than two hundred (200) milliseconds, then T1 will be lengthened by ten (10) milliseconds. This is done by adding ten (10) milliseconds to C1 which has been initially set at approximately two hundred ten (210) milliseconds as used in T1=(12.65*TR+C.–300) milliseconds. The same logic is applied to limit the ability of advancing T1 to approximately two hundred (200) milliseconds or less before the next R wave, in order to prevent the inflation valve of the lower leg cuffs from opening so late that not enough time remains for the deflation valves to open before the next R wave; keeping in mind the facts that the inflation valve for the thigh cuffs opens approximately fifty (50) milliseconds after T1 and remains open for approximately another one hundred (100) milliseconds, leaving only approximately fifty (50) milliseconds for the pair of deflation valves to open before the next R wave. Since the logic used in controlling the manual adjustment of the deflation valves sets a limit for the deflation to open no later than approximately thirty (30) milliseconds before the next R wave, it is clear that the deflation valves will have to open to the atmosphere within approximately thirty (30) milliseconds after the inflation valve of the thigh cuffs is closed.

The other manual inflation/deflation adjustment buttons 356, 358 work on the same principle; that is, with each depression of one of the buttons, the CPU will check the conditions limiting the timing of the valves, and if the limits are not reached, then the timing for the inflation/deflation valves can be advanced or retreated by subtracting or adding ten (10) milliseconds to C1 or C2 of the above equation and the equation T2=(TR-C2) milliseconds.

The formula used in calculating T1 is given by:

$$T_1=(12.65*\sqrt{T_R}+C_1-300)\ \text{ms}$$

where the constant 12.65 is used instead of 0.4 when converting the unit of TR from seconds to milliseconds, and C1 is a constant that is initially assigned with a value equal to two hundred ten (210) milliseconds. However, this value can be changed later by manual adjustment. The factor three hundred (300) milliseconds has been experimentally determined to be equal to the approximate maximum time it takes for the applied external pressure wave to travel from the lower leg to the aortic valves.

After T1 has been determined, it is comprised with a value of one hundred fifty (150) milliseconds. If T1 is less than one hundred fifty (150) milliseconds, it is then set to one hundred fifty (150) milliseconds. If T1 is larger than one hundred fifty (150) milliseconds, then the calculated value will be used. These procedures guarantee that the inflation valves will not open in less than one hundred fifty (150) milliseconds after the R wave. Even when T1 is set at one hundred fifty (150) milliseconds, the leading edge of the pressure wave will not arrive at the aortic root until approximately three hundred fifty (350) milliseconds after the R wave, taking into account the time required for the pulse to travel up from the peripheral vasculature to the root of the aorta.

Once the value of T1 has finally been determined, it is used to calculate T2 using the following formula:

$$T2=(TR-C2)\text{ ms}$$

where the constant C2 is initially set at one hundred sixty (160) milliseconds and can be increased or decreased later by manual adjustment. From this equation, it is clear that the deflation valves open one hundred sixty (160) milliseconds before the next R wave. C2, however, can be increased or decreased manually to achieve an optimal hemodynamic effect.

The logic used in the timing of the inflation/deflation valves fulfill two basic criteria: (1) the inflation valves must not be opened so that the pressure pulse wave reaches the root of the aorta during systole, forcing the aortic valve to close prematurely, thereby creating systolic loading; and (2) the deflation valves must be opened to the atmosphere before the next R wave to allow enough time for the air pressure in the cuffs to decay to zero so that there is no residual pressure causing a tourniquet effect. Finally, the inflation/deflation valves will not be operational when the heart rate is higher than one hundred twenty (120) beats per minute or lower than thirty (30) beats per minute.

The inflation/deflation valve timing logic controls the timing of external pressure applied to the lower legs and thighs of the patient. A diagram of how the inflation/deflation valves are connected to the compressor and air tank is shown in FIG. 9.

The inflation/deflation timing logic is divided into two main parts: (1) the initiation stage upon power up during which the inflation/deflation times are set up automatically; and (2) the operation stage during which the inflation and deflation time can be adjusted manually. The operations of these timing logic systems are controlled by a microprocessor, and no signal will be sent out to the inflation/deflation valve power supply when the heart rate is higher than one hundred twenty (120) beats per minute or lower than thirty (30) beats per minute.

As shown, there are three (3) inflation valves and three (3) deflation valves. One pair of inflation/deflation valves are for the calves, one pair for the lower thighs, and one pair for the upper thighs. The valves are normally open, and selectively closed when energized. Upon receipt of a signal from the inflation/deflation timing control, electrical power to the inflation valves will be switched on for a period of one hundred (100) milliseconds and will open them to the air tank. Similarly, upon receipt of the deflation valve signal, power to the deflation valves will be switched on for a period of one hundred twenty (120) milliseconds and will open the lower leg and thigh cuffs to the atmosphere. In addition, two safety valves can be provided, each of them located between the inflation valve and the cuffs. The safety valves are normally open to air. These two optional valves (not shown) are independent of the logic controlling the inflation/deflation valves. They are installed in case of power failure so that pressure remaining in the leg and thigh cuffs can be vented to the atmosphere automatically.

During initiation stage when power is turned on, the computer 214 of the control console 202 will start a series of initiation procedures. The first step is to maintain the deflation valves open to atmosphere. Each deflation valve will remain open for one hundred twenty (120) milliseconds, or long enough to relieve all the air pressure from the leg and thigh cuffs. The computer 219 will then look for the input of the electrocardiogram (ECG) and determine the presence of the QRS complex. If the QRS complex is not detected, the inflation/deflation valves 208, 210, 212 will not be activated and the external counterpulsation will not start. The inflation valves will remain open to atmosphere; no compressed gas will enter the inflatable devices 208, 210, 212 from the tank 236.

After the detection of four (4) complete R-R intervals, the CPU will determine their average (TR), and will update TR by taking the mean of the last TR and the new R-R interval. Meanwhile, the two constants used for the calculation of inflation time T1 and deflation time T2 will be initiated with the values C1=210 milliseconds and C2=160 milliseconds. Definitions of T1 and T2 and other variables are shown diagrammatically in the example of FIG. 29. They are:

TR(R-R interval): average R-R interval in ms.

T1 (inflation time): interval from R wave to the opening of lower leg inflation valve in ms. Note that the inflation valve for the thigh cuffs open twenty to seventy milliseconds, and preferably fifty milliseconds after T1. In addition, inflation valves are normally closed. However, they will be opened for a duration of one hundred milliseconds or more when energized.

TD(duration time): interval between the opening of the lower leg inflation valve and the opening of the deflation valves for both the lower legs and thighs in milliseconds.

T2(deflation time): interval from R wave to the opening of, the deflation valves in milliseconds. Note that the deflation valves for both lower leg and thigh cuffs are normally open to the atmosphere, but are selectively closed when energized. This opening time has been experimentally determined to be approximately at least forty (40) milliseconds longer than the pressure decay time T4.

T3(pressure rise time): interval between the time when the air pressure in the lower leg or thigh cuffs is zero (0) and the time when it reaches equilibrium with the pressure in the reservoir. This value has been measured experimentally under many different situations with various cuff sizes and is equal to approximately fifty (50) milliseconds.

T4(pressure decay time): interval for the air pressure in the cuffs to drop to zero when the deflation valves are opened to the atmosphere. The value of T4 has been determined in a variety of situations with various cuff sizes and has an average value of eighty (80) milliseconds.

Figure 29:
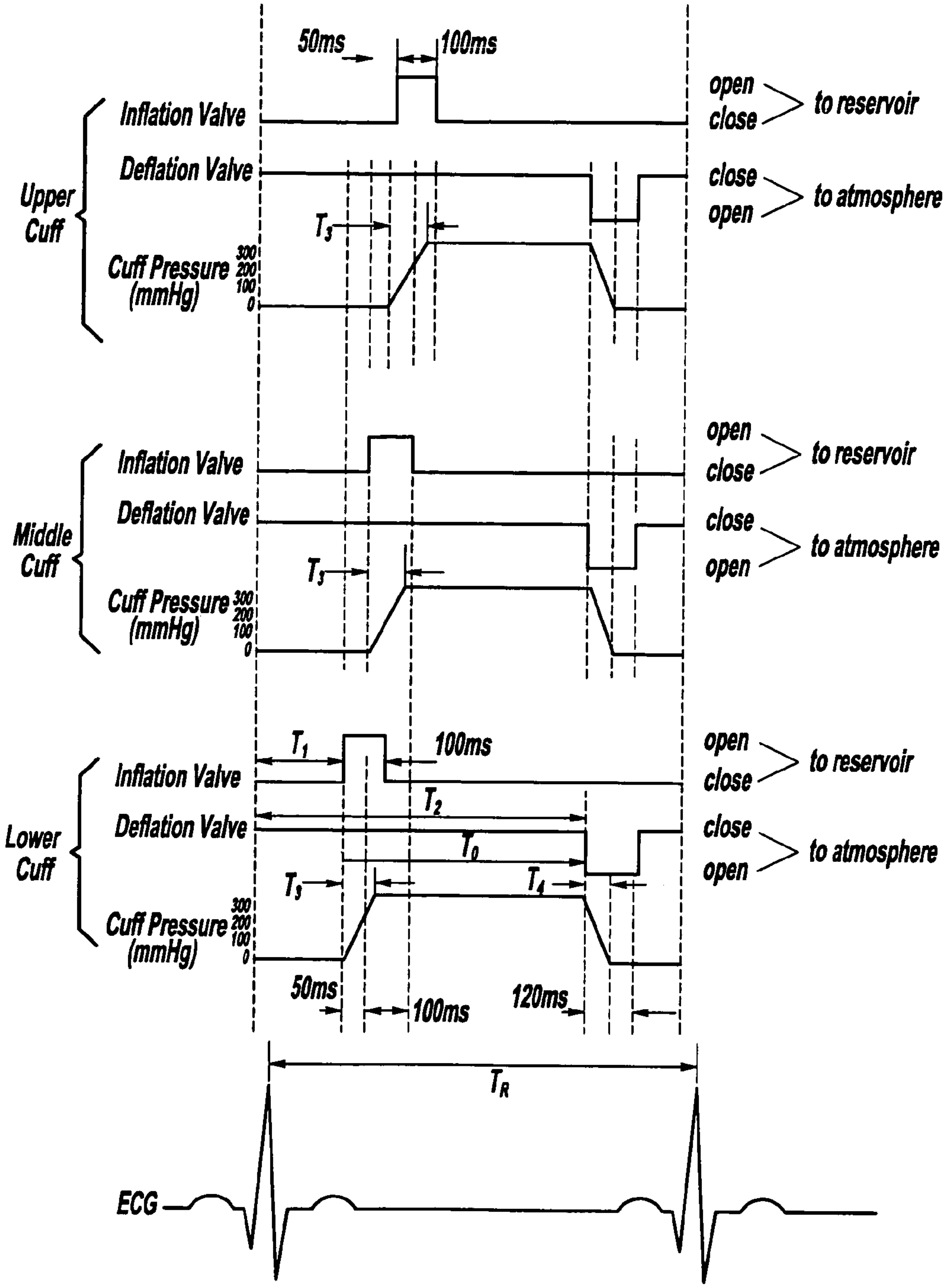
FIG. 29 is a diagrammatic representation of exemplary timing for the inflation/deflation valves and the air pressure waveforms in the inflatable devices of the external counterpulsation apparatus according to the present invention.

A diagrammatic representation of the time for inflation/deflation valves and air pressure waveforms for the three pair of cuffs shown in FIG. 29. The patient electrocardiogram (ECG) using a 3-lead system is digitized and the R-R interval TR determined. The R-wave is then used as a triggering signal. The inflation time T1 for the lower leg cuffs is calculated according to the square root formula of Bazett (see FDA 510(K) submission K882401, incorporated herein by reference):

$$T_1=(12.65*\sqrt{T_R}+C_1-300)\text{ ms}$$

where C1 is a constant with an initial value of two hundred ten (210) milliseconds. The inflation time can be adjusted manually, and the adjustment changes the C1 value. Therefore application of external pressure to the body begins with the lower leg T1 milliseconds after the ORS complex. Inflations of the lower thigh cuffs begin approximately twenty (20) to seventy (70) milliseconds, and preferably fifty (50) milliseconds after the inflation of the lower leg cuffs, and the upper thigh cuffs will be inflated approximately twenty (20) to seventy (70) milliseconds, and preferably fifty (50) milliseconds after the lower thigh cuffs.

The initial value assigned to T1 (as discussed above) is based on the square root formula of Bazett (Heart 7:353, 1920) which approximates the normal Q-T interval of the ECG as the product of a constant (0.4) times the square root of the R-R interval measured in seconds. The Q-T interval is measured from the beginning of the QRS complex to the end of the T wave. It represents the duration of ventricular electrical systole and varies with the heart rate; it can be used to approximate the hemodynamic systolic interval.

The foregoing discussion discloses and describes merely exemplary embodiments of the present invention for purposes of illustration. One skilled in the art will readily recognize from such discussion, and from the accompanying drawings and claims, that various changes, modifications, and variations can be made therein without departing from the principles, spirit or scope of the invention as defined in the following claims.

What is claimed is:

1. A method of controlling an external counterpulsation apparatus comprising:

selecting a patient treatment pressure;

outputting a signal corresponding to said selected treatment pressure;

detecting a pressure of a compressed fluid reservoir;

comparing said selected treatment pressure to said compressed fluid reservoir pressure; and controlling a pressure regulator valve based on a difference between said patient treatment pressure and said compressed fluid reservoir pressure.

2. The method according to claim 1, further comprising decreasing said compressed fluid reservoir pressure when said compressed fluid reservoir pressure is greater than a preset difference from said patient treatment pressure.

3. The method according to claim 2, wherein said compressed fluid reservoir pressure is decreased by venting said compressed fluid reservoir to atmosphere.

4. The method according to claim 1, further comprising increasing said compressed fluid reservoir pressure when said compressed fluid reservoir pressure is less than a preset difference from said patient treatment pressure.

5. The method according to claim 4, wherein said compressed fluid reservoir pressure is increased by operating a compressor.

6. The method according to claim 1, wherein said controlling includes damping to limit pressure swings beyond about 20 mm Hg of said selected treatment pressure.

7. The method according to claim 1, wherein said comparing includes comparing an output from a pressure transducer in said compressed fluid source reservoir to said selected treatment pressure.

8. The method according to claim 7, wherein said comparing includes translating an analog signal from said pressure transducer to a digital signal.

9. The method according to claim 1, further comprising controlling said compressed fluid reservoir pressure in an adjustment range of approximately one to ten psi.

10. The method according to claim 1, further comprising venting said pressure regulator valve to atmosphere during start-up of a compressor providing compressed fluid to said compressed fluid reservoir.

11. The method according to claim 1, further comprising venting said pressure regulator valve to atmosphere upon power failure.

12. The method according to claim 1, wherein said outputting a signal includes at least one of a digital voltage signal indicative of said selected pressure or a voltage proportional to said selected pressure.

* * * * *

UNITED STATES PATENT AND TRADEMARK OFFICE

CERTIFICATE OF CORRECTION

PATENT NO. : 7,314,478 B2 
APPLICATION NO. : 11/047509
DATED : January 1, 2008
INVENTOR(S) : John C. K. Hui It is certified that error appears in the above-identified patent and that said Letters Patent is hereby corrected as shown below:

<u>Column 3</u>,
Line 1, “Is” should be --is--.

<u>Column 4</u>,
Line 39, “is,” should be --is--.

<u>Column 5</u>,
Line 47, “portion 11” should be --portion II--.

<u>Column 6</u>,
Line 48, “portion 11” should be --portion II--.
Line 49, “portion 11” should be --portion II--.

<u>Column 11</u>,
Line 11, “Is” should be --is--.

<u>Column 12</u>,
Line 41, “Interface” should be --interface--.

<u>Column 14</u>,
Line 49, “ORS” should be --QRS--.

<u>Column 18</u>,
Line 25, “of,” should be --of--.
Line 58, “ORS” should be --QRS--.

Signed and Sealed this

Tenth Day of February, 2009

JOHN DOLL
*Acting Director of the United States Patent and Trademark Office*